United States Patent
Black

(10) Patent No.: US 9,551,711 B2
(45) Date of Patent: Jan. 24, 2017

(54) COMPOSITIONS AND METHODS FOR DETECTING NITRATION OF PKG-1α AND METHODS OF USE THEREOF

(71) Applicant: Augusta University Research Institute, Inc., Augusta, GA (US)

(72) Inventor: Stephen M. Black, Martinez, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 155 days.

(21) Appl. No.: 14/502,160

(22) Filed: Sep. 30, 2014

(65) Prior Publication Data
US 2015/0093759 A1     Apr. 2, 2015

Related U.S. Application Data

(60) Provisional application No. 61/885,635, filed on Oct. 2, 2013.

(51) Int. Cl.
| | |
|---|---|
| G01N 31/00 | (2006.01) |
| G01N 33/53 | (2006.01) |
| G01N 33/573 | (2006.01) |
| C07K 16/40 | (2006.01) |
| C07K 16/44 | (2006.01) |

(52) U.S. Cl.
CPC ............ *G01N 33/573* (2013.01); *C07K 16/40* (2013.01); *C07K 16/44* (2013.01); *C07K 2317/34* (2013.01); *G01N 2333/91205* (2013.01); *G01N 2440/00* (2013.01)

(58) Field of Classification Search
None
See application file for complete search history.

(56) References Cited

PUBLICATIONS

Aggarwal, et al.,"Attenuated vasodilatation in lambs with endogenous and exogenous activation of cGMP signaling: role of protein kinase G nitration", J Cell Physiol., 226 (12):3104-13 (2011).
Atkinson, et al., "1H NMR and circular dichroism studies of the N-terminal domain of cyclic GMP dependent protein kinase: a leucine/isoleucine zipper", Biochemistry, 30:9387-95 (1991).
Beckman, et al., "Oxidative chemistry of peroxynitrite", Methods Enzymol, 233:229-240 (1994).
Broughton, et al., "Chronic hypoxia augments depolarization-induced Ca2+ sensitization in pulmonary vascular smooth muscle through superoxide-dependent stimulation of RhoA", Am J Physiol., 298:L232-42 (2010).
Casteel, et al., "A crystal structure of the cyclic GMP-dependent protein kinase I{beta} dimerization/docking domain reveals molecular details of isoform-specific anchoring", J Biol Chem., 285:32684-8 (2010).
Chu, et al., "Activation by autophosphorylation or cGMP binding produces a similar apparent conformational change in cGMP-dependent protein kinase", J Biol Chem., 273:14649-56 (1998).
Corbin, et al., "Studies of two different intrachain cGMP-binding sites of cGMP-dependent protein kinase", J Biol Chem., 258:11391-7 (1983).
Corbin, et al., "Studies of cGMP analog specificity and function of the two intrasubunit binding sites of cGMP-dependent protein kinase", J Biol Chem., 261:1208-14 (1986).
Cruz, et al., "Chronic hypoxia induces right heart failure in caveolin-1-/- mice", Am J Physiol., 302:H2518-27 (2012).
Feil, et al., "Distribution of cGMP-dependent protein kinase type I and its isoforms in the mouse brain and retina", Neuroscience, 135:863-8 (2005).
Garbers, "Guanylyl cyclase receptors and their endocrine, paracrine, and autocrine ligands", Cell, 71:1-4 (1992).
Herranz, et al., "Integrin-linked kinase regulates vasomotor function by preventing endothelial nitric oxide synthase uncoupling: role in atherosclerosis", Circ Res., 110:439-49 (2012).
Hofmann, et al., "cGMP-dependent protein kinase. Autophosphorylation changes the characteristics of binding site 1", Eu J Biochem.,147:361-5 (1985).
Hofmann, et al., "Autophosphorylation of cGMP-dependent protein kinase is stimulated only by occupancy of one of the two cGMP binding sites", FEBS Letters 164:350-4 (1983).
Ischiropoulos, et al., "Peroxynitrite-mediated tyrosine nitration catalyzed by superoxide dismutase.", Archiv. Biochem. Biophys., 298:431-7 (1992).
Ischiropoulos, "Biological selectivity and functional aspects of protein tyrosine nitration",, Biochem Biophys Res Comm., 305:776-83 (2003).
Kawashima, et al., Endothelial NO synthase overexpression inhibits lesion formation in mouse model of vascular remodeling Arterioscler, Thromb Vas Biol., 21:201-7 (2001).
Khan, et al., "3-Nitrotyrosine in the proteins of human plasma determined by an ELISA method", Biochem. J., 330:795-801 (1998).
Kim, et al., "Co-crystal structures of PKG $I^2$ (92-227) with cGMP and cAMP reveal the molecular details of cyclic-nucleotide binding", PloS One, 6(4):e18413).
Klemm, et al., "Reduction of reactive oxygen species prevents hypoxia-induced CREB depletion in pulmonary artery smooth muscle cells", J Cardio Pharmacol, 58:181-91(2011).
Lincoln, et al., "Nitric oxide—cyclic GMP pathway regulates vascular smooth muscle cell phenotypic modulation: implications in vascular diseases", Acta Physiologica Scandinavica 164:507-15 (1998).
Madamanchi, et al., "Differential activation of mitogenic signaling pathways in aortic smooth muscle cells deficient in superoxide dismutase isoforms", Arterioscler, Thromb Vas Biol., 25:950-6 (2005).
Negash, et al., "Regulation of cGMP-dependent protein kinase-mediated vasodilation by hypoxia-induced reactive species in ovine fetal pulmonary veins", Am J of PhysiolLung Cell Mol Physicol..,293:L1012-20 (2007).
Nie, et al., "Endothelial nitric oxide synthase-dependent tyrosine nitration of prostacyclin synthase in diabetes in vivo", Diabetes 55, 3133-3141 (2006).

(Continued)

*Primary Examiner* — Lisa Cook
(74) *Attorney, Agent, or Firm* — Smith Gambrell & Russell LLP

(57) ABSTRACT

Antibodies for detecting nitration of nitrotyrosine 247 PKG-1α and antibodies for detecting nitrotyrosine 425 of PKG-1α are disclosed. Methods of detecting nitrotyrosine 247 PKG-1α and nitrotyrosine 425 of PKG-1α, and uses thereof are also disclosed for identification and diagnosis or phenotypes, pathologies, diseases and disorders associated with protein nitration of PKG-1α are also disclosed. In a preferred embodiment, one or more of the disclosed antibodies is used in the disclosed methods.

11 Claims, 7 Drawing Sheets

(56) References Cited

PUBLICATIONS

Nisbet, et al., "The role of NADPH oxidase in chronic intermittent hypoxia-induced pulmonary hypertension in mice", Am J Respir Cell Mol Biol., 40:601-9 (2009).

Nozik-Grayck, et al., "Role of reactive oxygen species in chronic hypoxia-induced pulmonary hypertension and vascular remodeling", Adv Exp Med Biol., 618:101-12 (2007).

Osborne, et al., "Crystal structure of cGMP-dependent protein kinase reveals novel site of interchain communication", Structure 19:1317-27 (2011).

Pilz, et al., "Role of cyclic GMP in gene regulation", Front Biosci., 10:1239-68 (2005).

Redondo-Horcajo, et al., "Cyclosporine A-induced nitration of tyrosine 34 MnSOD in endothelial cells: role of mitochondrial superoxide", Cardiovasc Res., 87:356-65 (2012).

Reed, et al., "Fast and slow cyclic nucleotide-dissociation sites in cAMP-dependent protein kinase are transposed in type Ibeta cGMP-dependent protein kinase", J Biol Chem., 271:17570-5 (1996).

Rudic, et al., "Direct evidence for the importance of endothelium-derived nitric oxide in vascular remodeling", J Clin Investig, 101:731-6 (1998).

Savvides, et al., "Crystal structure of the antioxidant enzyme glutathione reductase inactivated by peroxynitrite", J Biol Chem., 277:2779-84 (2002).

Takio, et al, "Guanosine cyclic 3',5'-phosphate dependent protein kinase, a chimeric protein homologous with two separate protein families", Biochemistry, 23:4207-18 (1984).

Uhler, "Cloning and expression of a novel cyclic GMP-dependent protein kinase from mouse brain", J Biol Chem., 268:13586-91 (1993).

Vaandrager, et al., "Molecular properties and biological functions of cGMP-dependent protein kinase II", Front Biosci ,10:2150-64 (2005).

Wang, et al., "Manganese superoxide dismutase inhibits neointima formation through attenuation of migration and proliferation of vascular smooth muscle cells", Free Radical Biology & Medicine, 52:173-81 (2012).

Wolfe, et al., "Cyclic nucleotides and disease", Curr Opin Cell Biol., 1:215-9 (1989b).

Wolfe, et al., "Characterization of a novel isozyme of cGMP-dependent protein kinase from bovine ao", J Biol Chem., 264:7734-41 (1989).

Zhao, et al., "Persistent eNOS activation secondary to caveolin-1 deficiency induces pulmonary hypertension in mice and humans through PKG nitration", J Clin Invest.,, 119:2009-18 (2009).

Zhao, et al., "Progressive cyclic nucleotide-induced conformational changes in the cGMP-dependent protein kinase studied by small angle X-ray scattering in solution", J Biol Chem., 272:31929-36 (1997).

COMPOSITIONS AND METHODS FOR DETECTING NITRATION OF PKG-1α AND METHODS OF USE THEREOF

CROSS-REFERENCE TO RELATED APPLICATIONS

This application claims benefit of and priority to U.S. Provisional Application No. 61/885,635, filed on Oct. 2, 2013, and which is incorporated by reference in its entity.

STATEMENT REGARDING FEDERALLY SPONSORED RESEARCH OR DEVELOPMENT

This invention was made with government support under Agreement Nos. HL60190, HL67841, HL084739 and HL0101902 awarded by the National Institutes of Health. The government has certain rights in the invention.

FIELD OF THE INVENTION

The invention is generally related to compositions for detecting nitration of nitration of PKG-1α and methods of use thereof to assist in the diagnosis of pathologies, diseases, and disorders associated therewith.

BACKGROUND OF THE INVENTION

PKG is a serine/threonine specific protein kinase that is activated upon the intracellular generation of 3',5' cyclic guanosine monophosphate (cGMP) by two main types of guanylyl cyclases (GC): soluble and membrane associated Garbers, D. L., *Cell* 71, 1-4 (1992)). Soluble GC acts downstream of NO, while the membrane associated GC is activated through the extracellular binding of natriuretic peptides (NP).

Tyrosine nitration is a selective process as not all tyrosine residues in a protein undergo nitration under patho-physiological conditions (Ischiropoulos, H., *Biochemical and Biophysical Research Communications* 305, 776-783 (2003)). PKG-1α has 21 tyrosine residues in its monomeric structure, of which 9 tyrosines are located in the regulatory domain and 12 are part of the catalytic domain. In vitro and in vivo studies have demonstrated that the nitration of cGMP-dependent protein kinase G-1α (PKG-1α) is an important posttranslational event responsible for the impaired PKG activity in the lungs of acute and chronic pulmonary hypertensive lambs (Aggarwal, S., et al., *Journal of Cellular Physiology* (2011)), mice with hypoxia-induced pulmonary hypertension (Negash, et al., *American Journal of Physiology* 293, L1012-1020 (2007)), and humans with idiopathic pulmonary arterial hypertension (Zhao, et al., *The Journal of Clinical Investigation* 119, 2009-2018 (2009)), however, the nature and location of this nitration along the PKG-1α protein is not known.

Accordingly, there remains a need for the identification and characterization of the tyrosine residues of PKG-1α that leads to pathological and disease states, and compositions and methods for detection thereof in biological samples.

Therefore, it is an object of the invention to provide the one or more tyrosine residues of PKG-1α that can be nitrated under physiological conditions.

It is another object of the invention to provide compositions and methods for the detection of these nitrated residues in a biological sample.

It is a further object of the invention to provide methods of use thereof for assisting in the diagnosis of diseases and disorders associated with nitration of PKG-1α.

SUMMARY OF THE INVENTION

It has been discovered that PKG-1α can be nitrated at tyrosine 247 and tyrosine 425. Antibodies for detecting nitration of nitrotyrosine 247 PKG-1α and antibodies for detecting nitrotyrosine 425 of PKG-1α are disclosed. Methods of detecting nitrotyrosine 247 PKG-1α and nitrotyrosine 425 of PKG-1α, and uses thereof are also disclosed. In a preferred embodiment, one or more of the disclosed antibodies is used in the disclosed methods.

For example, an antibody or antigen binding fragment thereof for detecting nitrated Y247 of PKG-1α can include an antigen binding site that binds specifically to an epitope within the amino acid sequence of SEQ ID NO:4, wherein the epitope includes the nitrated tyrosine 247 of SEQ ID NO:4. The antibody or antigen binding fragment thereof can bind to an amino acid sequence consisting of SEQ ID NO:5, or a fragment thereof including the nitrated tyrosine X. Antibodies that can bind to non-nitrated Y247 of PKG-1α are also disclosed. An antibody or antigen binding fragment thereof for detecting non-nitrated Y425 PKG-1α can include an antigen binding site that binds specifically to an epitope within the amino acid sequence of SEQ ID NO:1, wherein the epitope includes tyrosine 247 of SEQ ID NO:1.

An antibody or antigen binding fragment thereof for detecting Y425 PKG-1α can include an antigen binding site that binds specifically to an epitope within the amino acid sequence of SEQ ID NO:6, wherein the epitope includes the nitrated tyrosine 425 of SEQ ID NO:6. Antibodies that can bind to non-nitrated Y425 of PKG-1α are also disclosed. An antibody or antigen binding fragment thereof for detecting non-nitrated Y425 of PKG-1α can include an antigen binding site that binds specifically to an epitope within the amino acid sequence of SEQ ID NO:1, wherein the epitope includes tyrosine 425 of SEQ ID NO:1.

The antibodies can be monoclonal or a polyclonal, for example a rabbit polyclonal. The antigen binding fragment can be an Fv, Fab, Fab', or F(ab')$_2$ fragment. The antibody or antigen binding fragment thereof can be bispecific. The antibody or antigen binding fragment thereof can include a radioisotope, a fluorescent compound, a bioluminescent compound, biotin, chemiluminescent compound, a metal chelator, an enzyme, or a combination thereof.

Kits including the disclosed antibodies are also provided.

Methods of detecting nitrated PKG-1α comprising detecting nitration of PKG-1α at position Y247 of SEQ ID NO:4 or Y425 of SEQ ID NO:6 in a biological sample are also disclosed. In preferred embodiments, the detecting is carried out using mass spectrometry or an immune assay. The immunoassays can include detecting nitration of PKG-1α at position Y247 of SEQ ID NO:4 or SEQ ID NO:6 using the disclosed antibody or antigen binding fragment thereof that bind to nitrated Y247 or Y425 respectively. Preferred immunoassays include, but are not limited to, radioimmunoassays, ELISAs, immunoprecipitation assays, Western blot, fluorescent immunoassays, and immunohistochemistry.

The methods of detection can be employed to determine the propensity of a subject for developing or having a phenotype, pathology, disease or disorder associated with nitrated PKG-1α. Such methods typically include determining the level of nitrated Y247 or Y425 of PKG-1α by detecting nitrated Y247 or Y425 of PKG-1α in a biological sample obtain from the subject wherein a level of nitrated Y247 elevated compared to a control is indicative that the subject has or is likely to develop a phenotype, pathology, disease or disorder associated with nitrated PKG-1α.

Methods of diagnosing or assisting in the diagnosis of a phenotype, pathology, disease or disorder associated with nitrated PKG-1α can include determining the level of nitrated Y247 or Y425 of PKG-1α by detecting nitrated Y247 or Y425 of PKG-1α in a biological sample obtained from the subject wherein a level of nitrated Y247 or Y425 elevated compared to a control is indicative that the subject has or is likely to develop a phenotype, pathology, disease or disorder associated with nitrated PKG-1α.

Methods of selecting a subject for treatment of a phenotype, pathology, disease or disorder associated with nitrated PKG-1α include determining the level of nitrated Y247 or Y425 of PKG-1α by detecting nitrated Y247 or Y425 of PKG-1α in a biological sample obtained from the subject wherein the subject is selected for treatment if the level of nitrated Y247 or Y425 in the biological sample from the subject is elevated compared to a control.

Methods for determining the severity of a phenotype, pathology, disease or disorder associated with nitrated PKG-1α or for staging the progression of a phenotype, pathology, disease or disorder associated with nitrated PKG-1α can include (a) determining the level of nitrated Y247 or Y425, or detecting alterations in the expression levels of nitrated Y247 or Y425 in a biological sample from a subject by detecting nitrated Y247 or Y425; and (b) comparing the level of nitrated Y247 or Y425 in the biological sample to reference levels that correlate with disease severity or progression of a phenotype, pathology, disease or disorder associated with nitrated PKG-1α to determine the severity or progression of the a phenotype, pathology, disease or disorder associated with nitrated PKG-1α.

Suitable controls can be, for example, the average level of nitrated PKG-1α (e.g., nitrated Y247 or nitrated Y425, etc.) in subjects without a phenotype, pathology, disease or disorder associated with nitrated PKG-1α. The phenotype or pathology can be proliferation or a phenotype thereof, or an increase in expression of a marker thereof (e.g., vimentin expression, or nuclear levels of protein PCNA); increase in metabolic activity; decrease in expression of contractile markers such as MYH and Calponin-1; decrease a contractile phenotype (e.g., spinal shape morphology) or a marker thereof such as SM22-α, or localization thereof, for example to actin stress fibers; or any combination thereof in smooth muscle cells, such as vascular smooth muscle cells. The disease or disorder can be pulmonary hypertension, atherosclerosis, restenosis, hypoxia, vasoconstriction, vascular remodeling, or other vascular dysfunctions.

BRIEF DESCRIPTION OF THE DRAWINGS

FIG. 1A shows 3-NT/PKG-1α levels (Fold untreated) of wild type PKG-1α (WT), Y247F PKG-1α (Y247F) and Y425F PKG-1α (Y425F), with or without SIN-1, respectively. FIG. 1B shows PKG-1α activity (pmol/min/μg) of WT, Y247F and Y425F, with or without SIN-1, respectively. cGMP-independent PKG activity is indicated by white bars, cGMP dependent PKG activity is indicted by black bars. Data are mean±SEM, n=3, *p<0.05 vs. untreated WT-PKG-1α and Y425F-PKG-1α.

FIG. 4A shows 3-NT-Y247-PKG-1α levels (Fold WT-PKG-1α) of wild type PKG-1α (WT) and Y427F PKG-1α (Y247F), respectively, with or without SIN-1. FIG. 4B shows 3-NT-Y247-PKG-1α levels (Fold control) of lambs, without (Control) and with pulmonary hypertension secondary to increased pulmonary blood flow (Shunt), respectively. FIG. 4C shows 3-NT-Y247-PKG-1α/PKG-1α levels (Fold control) from humans without (Control) and with pulmonary hypertension (PH), respectively. Data are mean±SEM, n=4-5, *p<0.05 vs. untreated WT-PKG-1α for (A), control lambs for (B) and normal human lung for (C); † p<0.05 vs. WT-PKG-1α+SIN-1 (A).

FIG. 5A shows the results of AutoDock to dock two cGMP molecules to the cGMP binding sites (A and B) and an ATP molecule to the ATP binding site. FIG. 5B shows the comparison of the structure of PKG-1α and a homology model of PKG-1α produced by the YASARA software. FIG. 5C shows prediction of the affinity of cGMP for the cGMP binding site B in the PKG-1α homology model under control conditions. FIG. 5D shows an equivalent model under nitrative stress conditions (D). The addition of a NO2 group to Y247 is predicted to decrease the total hydrogen bonding energy between cGMP and PKG-1α from 91.93 kJ/mol to 54.02 kJ/mol (FIGS. 5C and 5D).

FIG. 6A shows [$^3$H]cGMP binding (% maximum WT-PKG-1α) over cGMP concentration (0-200 nM) for WT-PKG-1α (⊖), WT-PKG-1α with SIN-1(▼) Y247F-PKG-1α (⊟) and Y247F-PKG-1α+SIN-1(✶), respectively. FIG. 6B shows [$^3$H]cGMP dissociation (plotted as ln (B/B$_0$), with B$_0$ as the initial [$^3$H]cGMP bound] and B as the [$^3$H]cGMP remaining bound at time (S)) for WT-PKG-1α (⊖), WT-PKG-1α with SIN-1(▼) Y247F-PKG-1α (⊟) and Y247F-PKG-1α+SIN-1(✶), at various time points (0-200 seconds), respectively. FIG. 6C shows enzyme kinetics of the phosphor-transferase reaction of PKG-1α, plotted as PKG-1α activity (pmol/min/μg) for WT-PKG-1α (⊖), WT-PKG-1α with SIN-1(▼) Y247F-PKG-1α (⊟) and Y247F-PKG-1α+SIN-1(✶), at varying concentrations of cGMP (0-10 μM), respectively. Each value represents the mean of three separate experiments. Data are mean±SEM, n=3. *p<0.05 vs. untreated WT-PKG-1α.

DETAILED DESCRIPTION OF THE INVENTION

I. Definitions

Figure 1A:
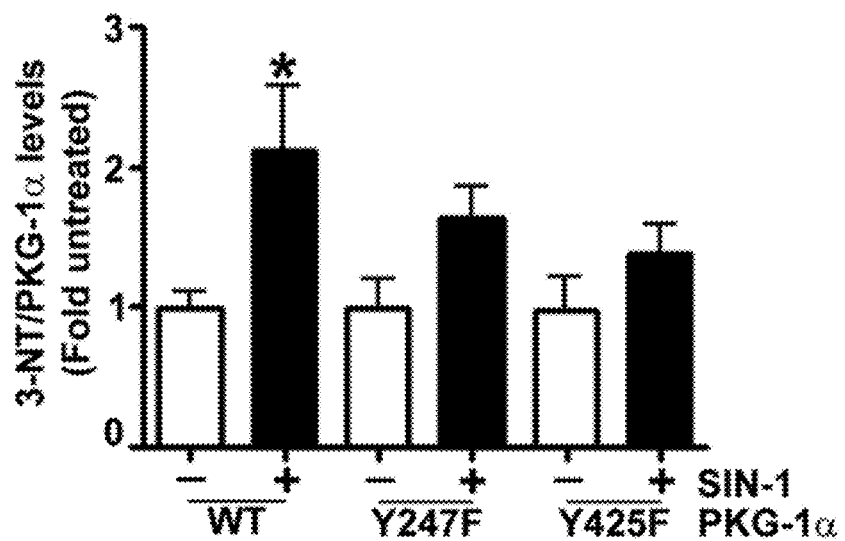
FIGS. 1A-1B are histograms.

As used herein, "treat" means to prevent, reduce, decrease, or ameliorate one or more symptoms, characteristics or comorbidities of an age-related disease, disorder or condition; to reverse the progression of one or more symptoms, characteristics or comorbidities of an age related disorder; to halt the progression of one or more symptoms, characteristics or comorbidities of an age-related disorder; to prevent the occurrence of one or more symptoms, characteristics or comorbidities of an age-related disorder; to inhibit the rate of development of one or more symptoms, characteristics or comorbidities or combinations thereof.

The terms "individual," "subject," and "patient" are used interchangeably herein, and refer to a mammal, including, but not limited to, rodents, simians, and humans.

The terms "reduce", "inhibit", "alleviate" and "decrease" are used relative to a control. One of skill in the art would readily identify the appropriate control to use for each experiment. For example a decreased response in a subject or cell treated with a compound is compared to a response in subject or cell that is not treated with the compound.

The terms "increase", "induce", "activate" and "improve" are used relative to a control. One of skill in the art would readily identify the appropriate control to use for each experiment. For example an increased response in a subject or cell treated with a compound is compared to a response in subject or cell that is not treated with the compound.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" can also mean the degree of sequence relatedness of a polypeptide compared to the full-length of a reference polypeptide. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M, and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "low stringency" refers to conditions that permit a polynucleotide or polypeptide to bind to another substance with little or no sequence specificity.

As used herein, the term "antibody" is used in the broadest sense unless clearly indicated otherwise. Therefore, an "antibody" can be naturally occurring or man-made such as monoclonal antibodies produced by conventional hybridoma technology. Antibodies include monoclonal and polyclonal antibodies as well as fragments containing the antigen-binding domain and/or one or more complementarity determining regions of these antibodies. Antibody refers to any form of antibody or antigen binding fragment thereof and includes monoclonal antibodies (including full length monoclonal antibodies), polyclonal antibodies, multispecific antibodies (e.g., bispecific antibodies), and antibody fragments.

As used herein, any form an "antigen" can be used to generate an antibody and encompasses single epitope, multiple epitopes, or the entire protein alone or in combination with one or more immunogenicity enhancing agents known in the art.

As used herein, the term "portion" refers to the minimal number of amino acids or nucleic acids, as appropriate, to constitute an immunogenic epitope of the antigen of interest.

As used herein, the terms "antigenic determinant" and "epitope" are used interchangeably refer to the structure recognized by an antibody.

As used herein, a "conformational epitope" is an epitope that includes discontinuous sections of the antigen's amino acid sequence. Antibodies bind a conformational epitope based on 3-D surface features, shape, or tertiary structure of the antigen.

As used herein, a "linear epitope" is an epitope that formed by a continuous sequence of amino acids from the antigen. Linear epitopes typically include about 5 to about 10 continuous amino acid residues. Antibodies bind a linear epitope based on the primary sequence of the antigen.

As used herein, the term "immunoassay" refers to an assay that uses an antibody or antibodies to specifically bind an antigen. The immunoassay is characterized by the use of specific binding properties of a particular antibody or antibodies to detect, quantify, and/or target the antigen.

As used herein, the term "Specific binding" between a binding agent, e.g., an antibody and a protein, for instance, a biomarker, refers to the ability of a capture- or detection-agent to preferentially bind to a particular agent that is present in a mixture; e.g., a biological sample. Specific binding also means a dissociation constant ($K_D$) that is less than about $10^{-6}$M; preferably, less than about $10^{-8}$ M; and, most preferably, less than about $10^{-9}$ M.

The phrase "specifically (or selectively) binds" to an antibody or "specifically (or selectively) immunoreactive with" when referring to a protein or peptide, refers to a binding reaction that is determinative of the presence of the protein in a heterogeneous population of proteins and other biologics. Thus, under designated immunoassay conditions, the specified antibodies bind to a particular protein or protein complex at least two times the background and do not substantially bind in a significant amount to other proteins present in the sample.

As used herein, a "label" or a "detectable moiety" is a composition detectable by spectroscopic, photochemical, biochemical, radiographic, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into nucleic acids, proteins and antibodies at any position. Any method known in the art for conjugating the antibody to the label may be employed, e.g., using methods described in Hermanson, Bioconjugate Techniques 1996, Academic Press, Inc., San Diego.

As used herein "antibody fragment" or "antigen binding fragment" of an antibody refers to at least a portion of the variable region of the immunoglobulin molecule that binds to its target, i.e., the antigen-binding region.

As used herein, the term "bispecific antibody" refers to an antibody, typically a monoclonal antibody, having binding specificities for at least two different antigenic epitopes.

II. Compositions

A. Identification of the Nitrated Residues of PKG-1α

The mammalian genome encodes a type 1 PKG (Feil, S., et al., *Neuroscience* 135, 863-868 (2005)) and a type 2 PKG (Uhler, M. D. The *Journal of Biological Chemistry* 268, 13586-13591 (1993); Vaandrager, et al., *Front Biosci* 10, 2150-2164 (2005)). Both type 1 and 2 PKG are homodimeric proteins containing two identical polypeptide chains of approximately 76 kD and 85 kD, respectively. Alternative mRNA splicing of PKG-1 produces a type 1α PKG (75 kD) and a type 1β PKG (78 kD), which only share 36% identity in their first 70-100 amino-terminal residues (Wolfe, L., et al., *Current Opinion in Cell Biology* 1, 215-219 (1989); Wolfe, L., et al., *The Journal of biological chemistry* 264, 7734-7741 (1989)). PKG-1 has been detected at high concentrations in all types of vascular smooth muscle cells (VSMC) (Feil, S., et al., *Neuroscience* 135, 863-868 (2005)). PKG-2 has been detected in renal, adrenal, intestinal, pancreatic and brain cells but not in cardiac and vascular cells.

The primary sequence of PKG-1α is divided into two separate domains: a regulatory domain (aa 1-343) containing an amino-terminal region (aa 1-110) and two cGMP binding sites (aa 111-343) and a catalytic domain (aa 344-671) containing an ATP-binding site (aa 344-474) and the substrate-binding site (aa 475-671) (Takio, K., et al; *Biochemistry* 23, 4207-4218 (1984)). The aminoterminal region of cGMP binding sites of PKG have different binding characteristics (Reed, R. B., et al., *The Journal of Biological Chemistry* 271, 17570-17575 (1996)); the amino-terminal high affinity site A and the succeeding low affinity site B display slow and fast cGMP-exchange characteristics, respectively (Hofmann, F., et al., *European Journal of Biochemistry/FEBS* 147, 361-365 (1985); Corbin, J. D., et al., *The Journal of Biological Chemistry* 258, 11391-11397 (1983). The binding of cGMP to these sites activates the enzyme. The occupation of site B decreases the dissociation of cGMP from site A, and therefore, site A shows positive cooperativity (Hofmann, F., et al., *European Journal of Biochemistry/FEBS* 147, 361-365 (1985). A maximally active enzyme is obtained when all four cGMP-binding sites of the dimeric kinase are occupied.

Full-length sequences for PKG-1α are known in the art. See, for example, UniProt Accession Number Q13976 (KGP1_HUMAN), which provides the amino acid sequence,

```
                                                            (SEQ ID NO: 1)
        MSELEEDFAK ILMLKEERIK ELEKRLSEKE EEIQELKRKL HKCQSVLPVP STHIGPRTTR

AQGISAEPQT YRSFHDLRQA FRKFTKSERS KDLIKEAILD NDFMKNLELS QIQEIVDCMY

PVEYGKDSCI IKEGDVGSLV YVMEDGKVEV TKEGVKLCTM GPGKVFGELA ILYNCTRTAT

VKTLVNVKLW AIDRQCFQTI MMRTGLIKHT EYMEFLKSVP TFQSLPEEIL SKLADVLEET

HYENGEYIIR QGARGDTFFI ISKGTVNVTR EDSPSEDPVF LRTLGKGDWF GEKALQGEDV

RTANVIAAEA VTCLVIDRDS FKHLIGGLDD VSNKAYEDAE AKAKYEAEAA FFANLKLSDF

NIIDTLGVGG FGRVELVQLK SEESKTFAMK ILKKRHIVDT RQQEHIRSEK QIMQGAHSDF

IVRLYRTFKD SKYLYMLMEA CLGGELWTIL RDRGSFEDST TRFYTACVVE AFAYLHSKGI

IYRDLKPENL ILDHRGYAKL VDFGFAKKIG FGKKTWTFCG TPEYVAPEII LNKGHDISAD

YWSLGILMYE LLTGSPPFSG PDPMKTYNII LRGIDMIEFP KKIAKNAANL IKKLCRDNPS

ERLGNLKNGV KDIQKHKWFE GFNWEGLRKG TLTPPIIPSV ASPTDTSNFD SFPEDNDEPP

PDDNSGWDID F.
``` the regulatory domain of PKG-1α contains a dimerization site, an autoinhibitory motif, and several autophosphorylation sites. The leucine zipper motif in the dimerization domain (aa 1-39) ensures substrate specificity of PKG-1α (Atkinson, R. A., et al., *Biochemistry* 30, 9387-9395 (1991)). The autoinhibitory region of PKG-1α (aa 58-72) binds to the catalytic domain and maintains the enzyme in an inhibited state. This auto-inhibition can be relieved by both cGMP binding and auto-phosphorylation which cause a conformational change (Zhao, J., et al., *The Journal of Biological Chemistry* 272, 31929-31936 (1997); Chu, D. M., et al., *The Journal of Biological Chemistry* 273, 14649-14656 (1998), and disrupts the auto-inhibitory interaction of the regulatory and catalytic domains. Cyclic GMP increases both the hetero-phosphorylation and the auto-phosphorylation activity of PKG (Hofmann, F., et al., *FEBS Letters* 164, 350-354 (1983)). The auto-phosphorylation of PKG-1α increases its cGMP-binding affinity and kinase activity (Hofmann, F., et al., *European Journal of Biochemistry/FEBS* 147, 361-365 (1985).

A hinge region connects the amino-terminal dimerization site with the two tandem cGMP binding sites: A (aa 111-227) and B (aa 228-343). These sites preferentially bind cGMP over cAMP with more than a 100-fold selectivity. The two It has been discovered that Y247 and Y425 of PKG-1α can be nitrated. Mass spectroscopy analysis, discussed in the Examples below, of the human 3-NT modified PKG-1α sequence, LADVLEETHYENGEYIIR (SEQ ID NO:2), corresponding to the peptide having the amino acids 233-250 (dash underlined in SEQ ID NO:1 above), and the sequence, QIMQGAHSDFIVRLYR (SEQ ID NO:3), corresponding to the peptide having the amino acids 411-426 (dash underlined in SEQ ID NO:1 above), demonstrated the nitration of Y247 (bolded and italicized in the sequences above) and Y425 (bolded and italicized in the sequences above).

It has also been discovered that that nitration of tyrosine 247, located within the cGMP binding site B of the regulatory domain of PKG-1α, is responsible for the impaired kinase activity.

Cyclic GMP binding to both sites A and B of PKG brings about a conformational change necessary for full kinase activity. The two cGMP binding sites share approximately 37% amino acid sequence similarity but differ in their cGMP binding kinetics (Corbin, J. D., et al., *The Journal of Biological Chemistry* 261, 1208-1214 (1986). This difference may be due to the number of hydrogen bonds between cGMP and the cGMP binding sites on PKG as well as the length of these bonds (Kim, J. J., et al., *PloS One* 6, e18413).

The Examples below show that molecular dynamic simulations using a full-length PKG-1α homology model indicated that the nitration of Y247 impairs hydrogen bonding between cGMP and the cGMP binding site B of the kinase. These results were confirmed by in vitro [$^3$H]cGMP binding studies and illustrate the mechanism by which PKG is believed to be regulated by nitrative stress. Nitrative stress only decreased the cGMP dependent kinase activity, while basal PKG activity was unchanged.

The Examples also show that nitration of tyrosine 247 occurs in vitro and in vivo, and nitration of tyrosine 247 can have biochemical, morphological, and pathological consequences.

Residues of PKG-1α that can be nitrated under physiological condition are provided with reference to SEQ ID NO:1. However, it will be appreciated that one of skill in art the can identify the corresponding residues in homologs, orthologs, paralogs, variants, etc., using one or more known techniques including but not limited to sequence alignment, structure alignment, etc., B. Antibodies for Identifying Nitrated PKG-1α

Antibodies and antigen binding fragments thereof that bind to a nitratable epitope on PKG-1α are disclosed.

Any specific antibody can be used in the methods and compositions provided herein. The term antibody encompasses a molecule including at least one variable region from a light chain immunoglobulin molecule and at least one variable region from a heavy chain molecule that in combination form a specific binding site for the target antigen. The antibody can be polyclonal or monoclonal. The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison et al., Proc. Natl. Acad. Sci. USA 81: 6851-6855 (1984)).

The antibody can be an IgG antibody. For example, the antibody can be a IgG1, IgG2, IgG3, or IgG4 antibody. An antibody can be in the form of an antigen binding antibody fragment including a Fab fragment, F(ab')$_2$ fragment, a single chain variable region, and the like. Fragments of intact molecules can be generated using methods well known in the art and include enzymatic digestion and recombinant means.

The region of the antibody that binds specifically to the target epitope can be referred to as the antigen binding site. Any form an antigen can be used to generate an antibody. Thus, the eliciting antigen may be a single epitope, multiple epitopes, or the entire protein alone or in combination with one or more immunogenicity enhancing agents known in the art. The eliciting antigen may be an isolated full-length protein or a fragment thereof. The antigen may be produced in a genetically modified cell. The DNA encoding the antigen can be genomic or non-genomic (e.g., cDNA). Any genetic vectors suitable for transformation of the cells of interest may be employed, including but not limited to adenoviral vectors, plasmids, and non-viral vectors, such as cationic lipids.

The antibody can be a bispecific antibody having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., Nature 305:537-39 (1983). Alternatively, bispecific antibodies can be prepared using chemical linkage. See, e.g., Brennan, et al., Science 229:81 (1985). Bispecific antibodies include bispecific antibody fragments. See, e.g., Hollinger, et al., Proc. Natl. Acad. Sci. U.S.A. 90:6444-48 (1993), Gruber, et al., *J. Immunol.* 152:5368 (1994).

The antibody or antigen binding fragment thereof can be labeled with a detectable marker or conjugated to a second molecule. Suitable detectable markers include, but are not limited to, a radioisotope, a fluorescent compound, a bioluminescent compound, biotin, chemiluminescent compound, a metal chelator or an enzyme.

1. Preparation of Antigens

Antibodies and antigen binding fragments thereof are typically prepared using methods known, some of which are discussed more detail below. The antibody includes an antigen binding site that binds to an epitope of PKG-1α that includes a nitratable tyrosine. As discussed above, PKG-1α can be nitrated at Y247 and Y425 of SEQ ID NO:1. Therefore, the disclosed antibodies and antigen binding fragments thereof typically bind to an epitope that includes Y247 or Y425 of SEQ ID NO:1, or the corresponding residue in a homolog, ortholog, paralog, or variant thereof.

In some embodiments, the antibody or antigen binding fragment thereof binds to a linear epitope that includes 4, 5, 6, 7, 8, 9, 10, 11, or more continuous amino acids an SEQ ID NO:1 including Y247 or Y425 of SEQ ID NO:1 numbered from the N-terminal methionine, or the corresponding residue in a homolog, ortholog, paralog, or variant thereof.

The antibody or antigen binding fragment thereof can bind a conformational epitope that includes a 3-D surface feature, shape, or tertiary structure of PKG-1α that includes Y247 or Y425 of SEQ ID NO:1 numbered from the N-terminal methionine, or the corresponding residue in a homolog, ortholog, paralog, or variant thereof. Therefore, in some embodiments, the epitope does not have a sequence that is a fragment of the primary sequence of SEQ ID NO:1.

In some embodiments the antibody or antigen binding fragment binds specifically to an epitope within the protein encoded by the amino acid sequence of SEQ ID NO:1, where the epitope includes the nitrated tyrosine at position 247 or at position 425 of SEQ ID NO:1. In certain embodiments the antibody can only bind to the protein encoded by the amino acid sequence of SEQ ID NO:1 if the tyrosine at position 247 or at position 425 is nitrated. For example, the antibody cannot bind to the protein encoded by the amino acid sequence of SEQ ID NO:1 if the tyrosine at position 247 or at position 425 is not nitrated.

It will be appreciated that an antibody or antigen binding fragment thereof can be created that binds to a nitrated or non-nitrated epitope. For antibodies that bind to nitrated PKG-1α, the epitope to which the antibody or antigen binding fragment thereof binds is a nitrated residue. For antibodies that bind to non-nitrated PKG-1α, the epitope is not nitrated. Therefore, for antibodies that bind to nitrated PKG-1α, the antigen used to prepare the antibody or antigen binding fragment thereof includes the nitrated residue of the target epitope. For antibodies that bind to non-nitrated PKG-1α, the antigen used to prepare the antibody or antigen binding fragment thereof does not includes nitrated residues. Antibodies that bind to non-nitrated PKG-1α can be used, for example, as control antibodies, to determine the specificity of the antibodies that bind to nitrated PKG-1α. In a preferred embodiment, antibodies that bind to nitrated PKG-1α and antibodies that bind to non-nitrated PKG-1α are prepared using an antigen having the same primary amino acid sequence and differ only in that the tyrosine of interest is nitrated or not nitrated, respectively.

As discussed in more detail below, methods of making antigens and using them to prepare antibodies are known in the art. Methods of preparing nitrated peptides are also known in the art. Nitrated peptides for use as antigens in preparing antibodies that bind nitrated PKG-1α can be prepared using peptide synthesis methods including, but not limited to liquid-phase synthesis and solid-phase synthesis; by in vivo recombinant protein expression; and by cell free synthesis. For example, nitration can be carried out during peptide synthesis, wherein the tyrosine amino acid monomer is nitrated tyrosine.

The peptide antigen can be prepared with a non-nitrated tyrosine which is nitrated before being used as an antigen. Nitration of the peptide can be carried out in vitro using a protein nitrating agent according to known methods. See, for example, Khan, et al., *Biochem. J.*, 330, 795-801 (1998), which describes in vitro preparation of nitrated bovine serum albumin and other plasma proteins using peroxynitrite. Briefly, peroxynitrite was prepared by Beckman, et al., *Methods in Enzymol*, 233, 229±240 (1994). Nitrated proteins were prepared by three additions of an alkaline stock solution of peroxynitrite to a final concentration of 1 mM (Beckman, et al., *Methods in Enzymol*, 233, 229±240 (1994)). Proteins were dialysed against three changes of PBS and the 3-nitrotyrosine content of BSA was determined by absorbance at 438 nm at pH 9.0 using a molar extinction coefficient of 4300 $M^{-1}$ $cm^{-1}$ according to Ischiropoulos, et al., *Archiv. Biochem. Biophys.*, 298:431-437 (1992) and was determined to be in the range of 3-6 mol nitrotyrosine/mol protein.

In some embodiments, the antigen includes one or more non-amino acid elements, one or more additional post-translation modifications, or a combination thereof. Examples of post-translational modifications include, but are not limited to glycosylation, phosphorylation, acetylation, citrullination and ubiquitination.

2. Exemplary Antigens for Preparing Antibodies Specific for Y247 Nitrated PKG-1α

Antigens for preparing an antibody or an antigen binding fragment thereof for detecting Y247 nitrated PKG-1α binds an epitope of SEQ ID NO:1 including nitrated Y247 are disclosed. The antigen can include the amino acid sequence

```
                                            (SEQ ID NO: 4)
MSELEEDFAK ILMLKEERIK ELEKRLSEKE EEIQELKRKL

HKCQSVLPVP STHIGPRTTR AQGISAEPQT YRSFHDLRQA

FRKFTKSERS KDLIKEAILD NDFMKNLELS QIQEIVDCMY

PVEYGKDSCI IKEGDVGSLV YVMEDGKVEV TKEGVKLCTM

GPGKVFGELA ILYNCTRTAT VKTLVNVKLW AIDRQCFQTI

MMRTGLIKHT EYMEFLKSVP TFQSLPEEIL SKLADVLEET

HYENGEXIIR QGARGDTFFI ISKGTVNVTR EDSPSEDPVF

LRTLGKGDWF GEKALQGEDV RTANVIAAEA VTCLVIDRDS

FKHLIGGLDD VSNKAYEDAE AKAKYEAEAA FFANLKLSDF
```

```
                        -continued
NIIDTLGVGG FGRVELVQLK SEESKTFAMK ILKKRHIVDT

RQQEHIRSEK QIMQGAHSDF IVRLYRTFKD SKYLYMLMEA

CLGGELWTIL RDRGSFEDST TRFYTACVVE AFAYLHSKGI

IYRDLKPENL ILDHRGYAKL VDFGFAKKIG FGKKTWTFCG

TPEYVAPEII LNKGHDISAD YWSLGILMYE LLTGSPPFSG

PDPMKTYNII LRGIDMIEFP KKIAKNAANL IKKLCRDNPS

ERLGNLKNGV KDIQKHKWFE GFNWEGLRKG TLTPPIIPSV

ASPTDTSNFD SFPEDNDEPP PDDNSGWDID F
``` where "X" is a nitrated tyrosine (i.e., 3-nitrotyrosine), or a homolog, an ortholog, a paralog, or a variant thereof where the tyrosine corresponding to X247 of SEQ ID NO:4 is a nitrated tyrosine (i.e., 3-nitrotyrosine).

In some embodiments, the antigen is a fragment of SEQ ID NO:4 including X247, or a fragment of a homolog, an ortholog, a paralog, or a variant thereof including the tyrosine corresponding to X247 of SEQ ID NO:4. For example, the fragment of SEQ ID NO:4 can have any integer between 5 and 670 (inclusive) of continuous amino acids of SEQ ID NO:4 including X247 of SEQ ID NO:4. The fragment of a homolog, an ortholog, a paralog, or a variant of SEQ ID NO:4 can have any integer between 5 and 670 (inclusive) of continuous amino acids of the homolog, an ortholog, a paralog, or a variant of SEQ ID NO:4 including the tyrosine corresponding to X247 of SEQ ID NO:4. a sequence that is a fragment of the primary sequence of SEQ ID NO:1.

In some embodiments the antibody or antigen binding fragment binds specifically to an epitope within the protein encoded by the amino acid sequence of SEQ ID NO:4, where the epitope includes the nitrated tyrosine 247 of SEQ ID NO:4. In certain embodiments the antibody can only bind to the protein encoded by the amino acid sequence of SEQ ID NO:4 if the tyrosine at position 247 is nitrated. For example, the antibody cannot bind to the protein encoded by the amino acid sequence of SEQ ID NO:4 if the tyrosine at position 247 is not nitrated.

In a particular embodiment, the antigen includes a fragment of SEQ ID NO:2 including or consisting of the amino acid sequence ENGEXIIRQGARGDC (SEQ ID NO:5) where "X" is a nitrated tyrosine (i.e., 3-nitrotyrosine), or a functional fragment or variant thereof that is sufficient to serves as an epitope of an antibody or antigen binding fragment thereof that recognizes X247 of SEQ ID NO:4. For example, the fragment can include or consist of 4, 5, 6, 7, 8, 9, 10, 11, or more continuous amino acids, preferably at least 5 continuous amino acids, of SEQ ID NO:5 including X5 of SEQ ID NO:5.

In some embodiments the antigen is a fusion protein that consists of SEQ ID NO:5 or a functional fragment or variant thereof fused to a heterologous amino acid sequence.

Also disclosed is an the antigen that includes a fragment of SEQ ID NO:1 including or consisting of the amino acid sequence ENGEYIIRQGARGDC (SEQ ID NO:8) where the tyrosine is not-nitrated, or a functional fragment or variant thereof that is sufficient to serves as an epitope of an antibody or antigen binding fragment thereof that recognizes non-nitrated Y247 of SEQ ID NO:1, and does not bind to an epitope of SEQ ID NO:5 including X5. For example, the fragment can include or consist of 4, 5, 6, 7, 8, 9, 10, 11, or more continuous amino acids, preferably at least 5 continuous amino acids, of SEQ ID NO:8 including Y5 of SEQ ID NO:8, and does not bind to an epitope of SEQ ID NO:5 including X5. In some embodiments, this antibody is use to identify PKG-1α that is not nitrated at Y247 of SEQ ID NO:1. In some embodiments it can serve as a control antibody.

In some embodiments the antigen includes one or more moieties of other elements. For example, the additional elements or moieties can increase the antigenicity or immunogenicity of the antigen. Methods of increasing antigenicity and immunogenicity of synthetic peptides are reviewed in Van Regenmortel, *Biologicals*, 29(3-4):209-13 (2001).

An rabbit polyclonal antibody raised against a synthetic peptide consisting of SEQ ID NO:5 is exemplified in the working Examples below.

3. Exemplary Antigens for Preparing Antibodies Specific for Y425 Nitrated PKG-1α

Antigens for preparing an antibody or an antigen binding fragment thereof for detecting Y425 nitrated PKG-1α binds an epitope of SEQ ID NO:1 including nitrated Y425 are disclosed. The antigen can include the amino acid sequence

```
                                              (SEQ ID NO: 6)
MSELEEDFAK  ILMLKEERIK  ELEKRLSEKE  EEIQELKRKL

HKCQSVLPVP  STHIGPRTTR  AQGISAEPQT  YRSFHDLRQA

FRKFTKSERS  KDLIKEAILD  NDFMKNLELS  QIQEIVDCMY

PVEYGKDSCI  IKEGDVGSLV  YVMEDGKVEV  TKEGVKLCTM

GPGKVFGELA  ILYNCTRTAT  VKTLVNVKLW  AIDRQCFQTI

MMRTGLIKHT  EYMEFLKSVP  TFQSLPEEIL  SKLADVLEET

HYENGEYIIR  QGARGDTFFI  ISKGTVNVTR  EDSPSEDPVF

LRTLGKGDWF  GEKALQGEDV  RTANVIAAEA  VTCLVIDRDS

FKHLIGGLDD  VSNKAYEDAE  AKAKYEAEAA  FFANLKLSDF

NIIDTLGVGG  FGRVELVQLK  SEESKTFAMK  ILKKRHIVDT

RQQEHIRSEK  QIMQGAHSDF  IVRLXRTFKD  SKYLYMLMEA

CLGGELWTIL  RDRGSFEDST  TRFYTACVVE  AFAYLHSKGI

IYRDLKPENL  ILDHRGYAKL  VDFGFAKKIG  FGKKTWTFCG

TPEYVAPEII  LNKGHDISAD  YWSLGILMYE  LLTGSPPFSG

PDPMKTYNII  LRGIDMIEFP  KKIAKNAANL  IKKLCRDNPS

ERLGNLKNGV  KDIQKHKWFE  GFNWEGLRKG  TLTPPIIPSV

ASPTDTSNFD  SFPEDNDEPP  PDDNSGWDID  F
``` where "X" is a nitrated tyrosine (i.e., 3-nitrotyrosine), or a homolog, an ortholog, a paralog, or a variant thereof where the tyrosine corresponding to X425 of SEQ ID NO:6 is a nitrated tyrosine (i.e., 3-nitrotyrosine).

In some embodiments, the antigen is a fragment of SEQ ID NO:6 including X425, or a fragment of a homolog, an ortholog, a paralog, or a variant thereof including the tyrosine corresponding to X425 of SEQ ID NO:6. For example, the fragment of SEQ ID NO:6 can have any integer between 5 and 670 (inclusive) of continuous amino acids of SEQ ID NO:6 including X425 of SEQ ID NO:6. The fragment of a homolog, an ortholog, a paralog, or a variant of SEQ ID NO:6 can have any integer between 5 and 670 (inclusive) of continuous amino acids of the homolog, an ortholog, a paralog, or a variant of SEQ ID NO:6 including the tyrosine corresponding to X425 of SEQ ID NO:2.

For example, the fragment can include or consist of 4, 5, 6, 7, 8, 9, 10, 11, or more continuous amino acids, preferably at least 5 continuous amino acids, of SEQ ID NO:6 including X425 of SEQ ID NO:6.

In some embodiments the antibody or antigen binding fragment binds specifically to an epitope within the protein encoded by the amino acid sequence of SEQ ID NO:6, where the epitope includes the nitrated tyrosine 425 of SEQ ID NO:6. In certain embodiments the antibody can only bind to the protein encoded by the amino acid sequence of SEQ ID NO:6 if the tyrosine at position 425 is nitrated. For example, the antibody cannot bind to the protein encoded by the amino acid sequence of SEQ ID NO:6 if the tyrosine at position 425 is not nitrated.

In some embodiments the antigen is a fusion protein that consists of between about 5-100 (inclusive) SEQ ID NO:6 or a functional fragment or variant thereof including X425 fused to a heterologous amino acid sequence.

In some embodiments the antigen includes one or more moieties of other elements. For example, the additional elements or moieties can increase the antigenicity or immunogenicity of the antigen. Methods of increasing antigenicity and immunogenicity of synthetic peptides are reviewed in Van Regenmortel, *Biologicals*, 29(3-4):209-13 (2001).

C. Antibody Compositions

To prepare an antibody that specifically binds to a nitrated PKG-1α protein purified, nitrated PKG-1α protein, or fragments, or epitopes thereof, or purified polypeptides expressed from their nucleic acid sequences and subsequently nitrated can be used. Using the purified peptide, antibodies can be prepared using any suitable methods known in the art.

The antibodies disclosed herein can be generated in cell culture, in phage, or in various animals, including but not limited to cows, rabbits, goats, mice, rats, hamsters, guinea pigs, sheep, dogs, cats, monkeys, chimpanzees, apes. Therefore, in one embodiment, an antibody is a mammalian antibody.

Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, *Antibody Production: Essential Techniques* (Wiley, 1997); Shephard, et al., *Monoclonal Antibodies* (Oxford University Press, 2000); Goding, *Monoclonal Antibodies: Principles And Practice* (Academic Press, 1993); *Current Protocols In Immunology* (John Wiley & Sons, most recent edition).

The disclosed antibodies can be modified by recombinant means to increase greater efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. No. 5,624,821, U.S. Pat. No. 6,194,551, Application No. WO 9958572; and Angal, et al., *Mol. Immunol.* 30:105-08 (1993). The modification in amino acids includes deletions, additions, substitutions of amino acids. In some cases, such changes are made to reduce undesired activities, e.g., complement-dependent cytotoxicity.

Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to nitrated PKG-1α. See e.g., *Antibody Engineering: A Practical Approach* (Oxford University Press, 1996).

The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays. They can also be used to quantify nitrated PKG-1α.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies. Therefore, the disclosed antibodies contain at least the CDRs necessary to maintain DNA binding and/or interfere with DNA repair.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

A monoclonal antibody is obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies can be made using any procedure which produces monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

Antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

1. Human and Humanized Antibodies

Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all, of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a nonhuman antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies are preferably prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

The antibody can be bound to a substrate or labeled with a detectable moiety or both bound and labeled. The detectable moieties contemplated with the present compositions include fluorescent, enzymatic and radioactive markers.

2. Single-Chain Antibodies

Methods for the production of single-chain antibodies are well known to those of skill in the art. A single chain antibody is created by fusing together the variable domains of the heavy and light chains using a short peptide linker, thereby reconstituting an antigen binding site on a single molecule. Single-chain antibody variable fragments (scFvs, also referred to as "Fv") in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

3. Monovalent Antibodies

In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the F(ab')$_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')$_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

4. Hybrid Antibodies

The antibody can be a hybrid antibody. In hybrid antibodies, one heavy and light chain pair is homologous to that found in an antibody raised against one epitope, while the other heavy and light chain pair is homologous to a pair found in an antibody raised against another epitope. This results in the property of multi-functional valency, i.e., ability to bind at least two different epitopes simultaneously. Such hybrids can be formed by fusion of hybridomas producing the respective component antibodies, or by recombinant techniques. Such hybrids may, of course, also be formed using chimeric chains.

5. Conjugates or Fusions of Antibody Fragments

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Such coupling of the antibody or fragment with the therapeutic agent can be achieved by making an immunoconjugate or by making a fusion protein, or by linking the antibody or fragment to a nucleic acid such as an siRNA, comprising the antibody or antibody fragment and the therapeutic agent.

In some embodiments, the antibody is modified to alter its half-life. In some embodiments, it is desirable to increase the half-life of the antibody so that it is present in the circulation or at the site of treatment for longer periods of time. For example, it may be desirable to maintain titers of the antibody in the circulation or in the location to be treated for extended periods of time. Antibodies can be engineered with Fc variants that extend half-life, e.g., using Xtend™ antibody half-life prolongation technology (Xencor, Monrovia, Calif.). In other embodiments, the half-life of the anti-DNA antibody is decreased to reduce potential side effects. The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin.

D. Methods of Making Antibodies

The antibodies can be generated in cell culture, in phage, or in various animals, including but not limited to cows, rabbits, goats, mice, rats, hamsters, guinea pigs, sheep, dogs, cats, monkeys, chimpanzees, apes. Therefore, in one embodiment, an antibody is a mammalian antibody.

Methods of making antibodies using protein chemistry are also known in the art. One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. Alternatively, the peptide or polypeptide is independently synthesized in vivo as described above. Once isolated, these independent peptides or polypeptides may be linked to form an antibody or antigen binding fragment thereof via similar peptide condensation reactions.

For example, enzymatic ligation of cloned or synthetic peptide segments allow relatively short peptide fragments to be joined to produce larger peptide fragments, polypeptides or whole protein domains. Alternatively, native chemical ligation of synthetic peptides can be utilized to synthetically construct large peptides or polypeptides from shorter peptide fragments. This method consists of a two-step chemical reaction. The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site.

II. Detecting Nitration of PKG-1α and Methods of Use Thereof

As discussed above and illustrated in the Examples below, it has been discovered that Y247 and Y425 of PKG-1α can be nitrated. Nitration of at least tyrosine 247, located within the cGMP binding site B of the regulatory domain of PKG-1α, is responsible for the impaired kinase activity PKG-1α. The methods provided below are discussed with reference to nitration at Y247. However, it will be appreciated that one of skill in the art can carry out all of the methods provided herein with respect to Y425 as well. Accordingly, the methods provided herein are also disclosed with respect to detecting nitration at Y425.

In addition to its role in mediating the vasodilator effects of NO, PKG contributes to the maintenance of a contractile-like phenotype in SMC, and the suppression of PKG expression/activity in vitro induces a more synthetic, dedifferentiated phenotype (Lincoln, T., et al., *Acta Physiologica Scandinavica* 164, 507-515 (1998)).

The transition of vascular smooth muscle cells (VSMC) from a contractile to a proliferative phenotype appears to be an early event in various pathologies, such as pulmonary hypertension, atherosclerosis, and restenosis (Negash, S., et al., *American Journal of Physiology* 297, H304-312 (2009); Acampora, K. B., et al., *Annals of Vascular Surgery* 24, 116-126; Dusserre, E., et al., *Biochimica Et Biophysica Acta* 1212, 235-244 (1994)), and is associated with increased oxidative and nitrosative stress (Klemm, D. J., et al., *Journal of Cardiovascular Pharmacology* 58, 181-191; Madamanchi, N. R., et al., *Arteriosclerosis, Thrombosis, and Vascular Biology* 25, 950-956 (2005); Wang, J. N., et al., *Free Radical Biology & Medicine* 52, 173-181). ROS and RNS levels are increased in pulmonary hypertensive mice (Nisbet, R. E., et al., *American Journal of Respiratory Cell and Molecular Biology* 40, 601-609 (2009)), lambs (Aggarwal, S., et al., *Journal of Cellular Physiology* (2011)), and humans Zhao, et al., *The Journal of Clinical Investigation* 119, 2009-2018 (2009) and the increase in oxidative and nitrosative stress is implicated in both vasoconstriction (Broughton, B. R., et al., *American Journal of Physiology* 298, L232-242) and vascular remodeling (Nozik-Grayck, E., et al., *Advances in Experimental Medicine and Biology* 618, 101-112 (2007)).

Furthermore, the nitration and subsequent attenuation of PKG-1α catalytic activity appears to be an important pathological event underlying the development of vascular dysfunction in pulmonary hypertension and other vascular pathologies (Aggarwal, S., et al., *Journal of Cellular Physiology* (2011); Zhao, et al., *The Journal of Clinical Investigation* 119, 2009-2018 (2009); Herranz, B., et al., *Circulation Research* 110, 439-449). Studies have identified nitration and the ensuing attenuation of PKG-1α activity in the lungs of lambs with pulmonary hypertension secondary to increased pulmonary blood flow and in lambs with rebound pulmonary hypertension associated with the acute withdrawal of inhaled NO therapy (Aggarwal, S., et al., *Journal of Cellular Physiology* (2011)).

In addition, the nitration and subsequent attenuation of PKG activity in the right ventricle (RV) appears to be responsible for the deterioration of RV function in a mouse model of PH induced by chronic hypoxia (Cruz, J. A., et al., *American Journal of Physiology* 302, H2518-2527). The increase in protein nitration associated with hypoxia reduces PKG activity through changes at the transcriptional and post-translational levels (Negash, et al., *American Journal of Physiology* 293, L1012-1020 (2007)). The clinical relevance of PKG nitration has also been shown by the observation that patients with idiopathic pulmonary arterial hypertension have increased PKG nitration in their lungs with no noticeable alteration in PKG protein levels (Zhao, et al., *The Journal of Clinical Investigation* 119, 2009-2018 (2009)). Thus, the accumulated data indicate that the nitration-dependent impairment of PKG activity is an important event in the development of vascular dysfunction in pulmonary hypertension.

Accordingly, nitration Y247 in PKG-1α is a molecular marker of reduced PKG-1α activity. Detection of nitrated Y247 in PKG-1α can be used to identify, or assist in the identification of reduced PKG-1α activity in a subject and to identify subjects with or likely to develop molecular, biochemical, or pathological consequences of reduced PKG-1α activity. Detection of nitrated Y247 in PKG-1α can also be used to determine if a subject has or is likely to develop a disease or disorder associated with reduced PKG-1α activity, and to assist in its diagnosis.

A. Method of Detecting Nitrated Y247 in PKG-1α

Methods for detecting nitration of Y247 of PKG-1α are disclosed.

1. Biological Samples

A biological sample can be obtained from an individual for use in the methods and bioassays disclosed herein. In some embodiments, the sample is a tissue biopsy or cells obtained from the subject. The sample should be handled in accordance with the method of detection that will be employed. In some embodiments, a biological sample that is of tissue or cellular origin can be solubilized in a lysis buffer optionally containing a chaotropic agent, detergent, reducing agent, buffer, and salts. The conditions for handling biological samples that are analyzed for mRNA level may be different than the conditions for handling biological samples that are analyzed for protein level, and such conditions are known in the art.

The sample is preferably a biological fluid sample taken from a subject. Examples of biological samples include urine, barbotage, blood, serum, plasma, tears, saliva, cerebrospinal fluid, tissue, lymph, synovial fluid, or sputum etc. In a preferred embodiment, the biological fluid is whole blood, or more preferably serum or plasma. Serum is the component of whole blood that is neither a blood cell (serum does not contain white or red blood cells) nor a clotting factor. It is the blood plasma with the fibrinogens removed. Accordingly, serum includes all proteins not used in blood clotting (coagulation) and all the electrolytes, antibodies, antigens, hormones, and any exogenous substances (e.g., drugs and microorganisms). The sample can be diluted with a suitable diluent before the sample is analyzed.

The biological sample can be obtained from a tissue or organ that exhibits or will symptoms or is otherwise associated with a phenotype, pathology, disease, or disorder associated with reduced PKG-1α activity. For example, in some embodiments, the tissue is a lung sample (e.g., a lung biopsy) or a vascular biopsy.

2. Methods of Detection

Nitration of Y247 can be detected using immunodetection methods, mass spectroscopy, or high performance liquid chromatography (HPLC). In a preferred embodiment, the method includes detecting the level of nitrated Y247 of PKG-1α in protein isolated from cells of the subject.

a. Immunoassays

A preferred method includes immunoassays whereby nitrated Y247 is detected by its interaction with an antibody, or antigen binding fragment thereof specific for nitrated Y247, such as those disclosed herein. Nitrated Y247 can be detected in either a qualitative or quantitative manner. Exemplary immunoassays that can be used for the detection of nitrated Y247 include, but are not limited to, radioimmunoassays, ELISAs, immunoprecipitation assays, Western blot, fluorescent immunoassays, and immunohistochemistry, flow cytometry, protein arrays, multiplexed bead arrays, magnetic capture, in vivo imaging, fluorescence resonance energy transfer (FRET), and fluorescence recovery/localization after photobleaching (FRAP/FLAP).

Generally, a sample obtained from a subject can be contacted with the antibody. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or ProteinChip® array and can be analyzed by gas phase ion spectrometry as described above.

Immunoassays for the detection of nitrated Y247 include the ability to contact a biological sample with an antibody specific to nitrated Y247 under conditions such that an immunospecific antigen-antibody interaction may occur, followed by the detection or measurement of this interaction. The binding of the antibody to nitrated Y247 of PKG-1α protein thereof may be used to detect the presence and altered levels of nitrated Y247 of PKG-1α.

An immunoassay can include the steps of detecting and analyzing nitrated Y247 in a sample. For example, a method can include the steps of (a) providing an antibody that specifically binds to nitrated Y247; (b) contacting a sample with the antibody; and (c) detecting the presence of a complex of the antibody bound to the nitrated Y247 in the sample.

Typically, after incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and calorimetric labels such as colloidal gold or colored glass or plastic beads. Alternatively, the nitrated Y247 in the sample can be detected using an indirect assay, wherein, for example, a second, labeled antibody is used to detect bound anti-nitrated Y247 antibody, and/or in a competition or inhibition assay wherein, for example, a monoclonal antibody which binds to a distinct epitope of PKG-1α is incubated simultaneously with the mixture.

A common enzyme immunoassay is the "Enzyme-Linked Immunosorbent Assay (ELISA)." ELISA is a technique for detecting and measuring the concentration of an antigen using a labeled (e.g., enzyme linked) form of the antibody. There are different forms of ELISA, which are well known to those skilled in the art. Standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M., *J. Clin. Chem. Clin. Biochem.,* 22:895-904 (1984).

In a "sandwich ELISA", a first antibody, as referred to herein as the "capture" antibody is linked to a solid phase (i.e., a microtiter plate) and exposed to a biological sample containing antigen (e.g., PKG-1α). The solid phase is then washed to remove unbound antigen. A second antibody, as referred to herein as the "detection" antibody, is then bound to the bound-antigen (if present) forming an antibody-antigen-antibody sandwich. In preferred embodiments the second antibody is labeled (e.g., enzyme linked). In some embodiments, the solid phase is washed to remove unbound antibody, and treated with a third, labeled antibody that binds to and allows detection of the second antibody. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing the antigen (i.e., PKG-1α). The antigen-antibody mixture is then contacted with a solid phase (e.g., a microtiter plate) that is coated with antigen. The more antigen present in the sample, the less free antibody that will be available to bind to the solid phase. A labeled (e.g., enzyme linked) secondary antibody is then added to the solid phase to determine the amount of primary antibody bound to the solid phase.

Other techniques may be used to detect the biomarkers, according to a practitioner's preference, and based upon the present disclosure. One such technique is Western blotting (Towbin et al., *Proc. Nat. Acad. Sci.,* 76:4350 (1979)), wherein a suitably treated sample is run on an SDS-PAGE gel before being transferred to a solid support, such as a nitrocellulose filter. Detectably labeled antibodies that specifically bind to nitrated Y247 can then be used to assess levels of nitrated Y247, where the intensity of the signal from the detectable label corresponds to the amount of peptide present. Levels can be quantitated, for example by densitometry.

Assays and kits that include reagents for the detection and qualitative or quantitative measurement of nitrated Y247 in a subject's biological sample are also provided. For example, if detection of the nitrated Y247 is by means of ELISA, components of the assay or kit will include an antibody directed against nitrated Y247, in which the antibody may optionally be linked to an enzyme, fluorescent dye, radioactive label, etc.

It will be appreciated that some immunoassays, for example ELISAs, can require two different antibodies. In some embodiments, a first antibody is a nitrated Y247 specific antibody such as those disclosed herein and the second antibody is specific for nitrotyrosine or PKG-1α. Antibodies specific for nitrotyrosine and PKG-1α and known in the art and commercially available. In some embodiments, an anti-nitrated Y247 is used as the capture antibody and an anti-nitrotyrosine or an anti-PKG-1α is used as the detection antibody. In some embodiments, an anti-nitrotyrosine or anti-PKG-1α antibody is used as the capture antibody and an anti-nitrated Y247 is used as the detection antibody.

Immunoassays such as ELISA can also be used to distinguish nitrated Y247 from total PKG-1α or total nitrated PKG-1α. For example, as discussed above, PKG-1α is also nitrated at least at Y425. Therefore, in some embodiments, the assays are designed to measure nitration of Y427 relative to (1) total PKG-1α, (2) total nitrated PKG-1α, (3) or Y425 nitrated PKG-1α. For example, an anti-PKG-1α antibody can be used as the capture antibody. Captured samples are separately detected with anti-Y247 and anti-nitrotyrosine or a second anti-PKG-1α antibody to determine the level of Y247 nitration relative to total nitrated PKG-1α or total PKG-1α respectively.

b. Mass Spectrometry and Chromatography

Nitrated Y247 can also be detected using mass spectrometry, or any of various chromatography techniques including, but not limited to, gas, liquid, and affinity chromatography techniques, and combinations thereof. For example, in the Examples below Y247 and Y425 were detected by first immunoprecipitating total PKG-1α of biological sample, followed by gel electrophoresis, in-gel protein digestion, and MALDI-TOF mass spectrometry.

3. Controls

The methods disclosed herein typically include comparing the level of nitrated Y247 detected in a sample obtained from the subject to a control. Suitable control will be known to one of skill in the art. For example, controls can include, standards obtained from healthy subjects, such as subjects without nitrated Y247, or low levels of nitrated Y247, or subjects without phenotypes, pathologies, diseases or disorders associated with nitrated Y247. Reference indices can be established by using a series of subjects that have been diagnosed with a pathology, a disease or a disorder associated with nitrated Y247 and having different and known disease severities or prognoses. A control can be a single or more preferably pooled or averaged values of like individuals using the same assay. The control biological sample can be assayed for levels of nitrated Y247 using the same methods as the test sample.

B. Methods Identifying and Diagnosing Subject with Nitrated Y247 of PKG-1α

Method of identifying subjects with nitrated Y247 and diagnosing or assisting in the diagnosis of a phenotype, pathology, disease or disorder associated with nitrated PKG-1α or the likelihood of developing a phenotype, pathology, disease or disorder associated with nitrated PKG-1α are also disclosed.

1. Methods of Diagnosis

The propensity of the subject for developing or having phenotypes, pathologies, diseases or disorders associated with nitrated PKG-1α can be determined based on the level of nitrated Y247 of PKG-1α. If the level of nitrated Y247 is higher than a control, for example, the average level in subjects without a phenotype, pathology, disease or disorder associated with nitrated PKG-1α, the subject is more likely to develop a phenotype, pathology, disease or disorder associated with nitrated PKG-1α; or to have a phenotype, pathology, disease or disorder associated with nitrated PKG-1α.

Methods of selecting subjects for treatment for phenotypes, pathologies, diseases or disorders associated with nitrated PKG-1α are also disclosed. Typical the method includes determining the level of nitrated Y247 in a biological sample from the subject. If the level of nitrated Y247 is higher than a control, for example the average level in subjects without a phenotype, pathology, disease or disorder associated with nitrated PKG-1α, the subject can be selected for treatment.

An phenotype, pathology, disease or disorder associated with nitrated PKG-1α in an individual can be diagnosed or detected based on the level of nitrated Y247. If the level of nitrated Y247 is higher than a control, for example, the average level in subjects without a phenotype, pathology, disease or disorder associated with nitrated PKG-1α, the subject can be diagnosed with or is likely to develop the a phenotype, pathology, disease or disorder associated with nitrated PKG-1α.

Methods for determining the severity of a phenotype, pathology, disease or disorder associated with nitrated PKG-1α and for staging the progression of a phenotype, pathology, disease or disorder associated with nitrated PKG-1α are also disclosed. The methods can include (a) determining the level of nitrated Y247, or detecting alterations in the expression levels of nitrated Y247 in a biological sample from a subject; and (b) comparing the levels in the biological sample to reference levels that correlate with disease severity or progression of a phenotype, pathology, disease or disorder associated with nitrated PKG-1α to determine the severity or progression of the a phenotype, pathology, disease or disorder associated with nitrated PKG-1α.

2. Conditions to Identify or Diagnose a. Phenotypes and Pathologies

The Examples below show that exposure to the peroxynitrite generator, 3-morpholinosydnonimine N-ethylcarbamide (SIN-1) induced proliferation and metabolic activity in the PASMC expressing WT-PKG-1α but not in the cells transfected with the Y247F-PKG-1α mutant. Immunoblot analysis demonstrated that PASMC transfected with WT and Y247F-PKG-1α exhibited a contractile phenotype, as illustrated by the increased levels of the contractile markers: MYH and Calponin-1 and decreased levels of the proliferative marker, Vimentin. However, when exposed to SIN-1, WT-PKG-1α expressing PASMC acquired a more proliferative phenotype compared to the cells transfected with the Y247F-PKG-1α mutant.

The Examples also show that the PASMC transfected with the WT- and the Y247F-PKG-1α were spindle shaped and had increased expression of contractile phenotype marker, SM22-α, bound to actin stress fibers. In contrast, the nuclear levels of the proliferative marker protein, PCNA, were decreased in these cells. SIN-1 treatment attenuated SM-22α expression and increased PCNA staining in the WT- but not in the Y247F-PKG-α expressing cells indicating that the Y247F-PKG-α mutant is resistant to phenotype modulation by nitrosative stress.

Therefore, the methods of detecting nitrated Y247 can be used to identify or diagnosis PKG-1α nitration dependent phenotypes and pathologies in smooth muscle cells, particularly vascular smooth muscle cells. The methods can be used to identify or diagnosis, or assist in the identification or diagnosis of nitration-dependent increase in proliferation or a phenotype thereof, or an increase in expression of a marker thereof (e.g., vimentin expression, or nuclear levels of protein PCNA); increase in metabolic activity; decrease in expression of contractile markers such as MYH and Calponin-1; decrease a contractile phenotype (e.g., spinal shape morphology) or a marker thereof such as SM22-α, or localization thereof, for example to actin stress fibers; or any combination thereof b. Diseases and Disorders The Examples below show that nitration of PKG-1α is increased following SIN-1 treatment; high levels of Y247 nitration can be detected in the peripheral lung tissue of lambs with pulmonary hypertension secondary to increased pulmonary blood flow and Y247 nitration is increased in the pulmonary vessels from patients suffering from idiopathic pulmonary hypertension compared to controls. Taken together the Examples indicate that the nitration of Y247 is an important mechanism by which nitrative stress impairment of PKG-1α activity both in vitro and in vivo.

Accordingly, methods of detecting nitrated Y247 can be used to identify or diagnosis, or assist in the identification or diagnosis of nitration-dependent diseases or disorders including, but not limited to, pulmonary hypertension including idiopathic pulmonary arterial hypertension, atherosclerosis, restenosis, hypoxia, vasoconstriction, vascular remodeling, and other vascular dysfunctions.

3. Methods of Treatment

All of the methods disclosed herein can include a step of treating the subject for a phenotype, pathology, disease or disorder associated with nitration or increased nitration of Y247 of PKG-1α.

In some embodiments, the compositions and methods disclosed herein are used to establish, or modify a dosage regime. For example, the subject can be administered a first dose of the composition for a first dosing period; and a second dose of the composition for a second dosing period, optionally followed by one or more additional doses for one or more additional dosing periods. The first dosing period can be less than one week, one week, or more than one week. In some embodiments the dosage regime is a dose escalating dosage regime. The first dose can be a low dose. Dose escalation can be continued until a satisfactory biochemical or clinical response is reached, for example a reduction nitration of Y247 of PKG-1α in the subject. Next, the dosages can be maintained or steadily reduced to a maintenance dose. The methods can be used to standardize, optimize, or customize the dose level, dose frequency, or duration of the therapy.

III. Devices, Kits, and Assays for Detection of Nitrated Y247 of PKG-1α in a Subject Devices, kits, and assays for detection of nitrated Y247 or elevated levels thereof in a subject are also disclosed. The nitrated Y247 can be detected using a variety of test formats (e.g., assay, strip, etc.), and can be determined, in part by the type of biomolecular recognition element (e.g. antibodies, antigens, etc.) being used to detect the nitrated Y247. The marker being detected may be nitrated Y247 also or a combination of markers. The additional marker or markers being detected may be specific to one condition or multiple conditions.

Devices, kits, and assays can include a test or support surface used for performing a test for detecting the presence of nitrated Y247. The test or support surface may be coated with/hold the selected detection antibodies, etc. specific to nitrated Y247, nitrotyrosine, PKG-1α, etc.

The device, kit, or assay typically includes reagents and/or apparatus that can be used to carry out the test. Some devices, kits, or assays include an apparatus that includes a support surface for the detection of the marker. The surface, can be, for example a surface on which the selected detection antibodies, etc. can be coated/held for detection of the selected marker(s). In some embodiments, the test or support surface may be part of an assay having one or more containers (or wells). The test or support surface may be the inner surface of a well or container. The inner surface of one or more wells or containers may be coated with the detection antibody specific to the marker(s) being detected.

Any appropriate assay or ELISA (sandwich, indirect, competitive, reverse, etc.) can be provided as part of the kit or device. For example, the kits or device can provided a polystyrene microplate, having wells/containers with inner surfaces capable of being coated with antibody. These inner surfaces may or may not be treated with substances known in the art to promote or enhance coating. For example the surface can be a maxisorp, POLYSORP, medisorp, MINISORP or COVALINK surface. Each well or container may be white or opaque to allow for easier visualization of any color, or any visually detectable change, occurring in or on the well or container. It will be appreciated that the size, surface area, total and/or working volumes, appearance, and/or color/visual parameters and/or qualities can be modified as desired within the scope of the present disclosure.

In some embodiments, the test or support surface may be part of a vial (or container or well), a test strip, a chromatography substrate, a gene chip, a SNAP test, or any other diagnostic test or test system used for detecting markers. The test or support surface may be made of paper, plastic, glass, metal, etc. and take several forms such as paddle, beads, wells, electrodes, etc.

In some embodiments, non-specific adsorption to the test surfaces coated with the BRE (e.g. the detection antibody), such as the coated well/container of an assay, may be minimized by blocking the test surface with a blocking agent. The blocking agent may be one or more proteins, sugars and/or polymers such as bovine serum albumin, gelatin, polyethylene glycol, sucrose, etc.

The kit or device can include an appropriate biomolecular recognition element (BRE), for detection of the biomarker. In some embodiments, the test surface is coated with the BRE (e.g., the detection antibody). The coated surface, such as the coated well/container of an assay, may be coated with a preserving (or stabilizing) agent to preserve the activity of the test surface. Test surfaces coated with the BRE and the blocking agent may also be coated with the preserving agent. The preserving agent may allow the test surfaces coated with the preserving agent, and the BRE and/or blocking agent, to be stored for an extended period of time before use. Test surfaces coated with the preserving agent, and the BRE and/or blocking agent, may maintain immunological activity for several months compared to if no preserving agent is employed (where immunological activity of a test surface coated with the BRE and/or a blocking agent may continually decline over time).

In some embodiments, the marker being detected, when present in increased or increasing amounts, may indicate a positive/reactive result. In some embodiments, the marker being detected, when absent or present in decreased or decreasing amounts, may indicate a positive/reactive result.

To detect if a marker is present in a sample, a signal from the sample may be compared against the signals of a high standard and a low standard which can be included with the kit or device. A qualitative/visual signal may be generated or visualized of the sample and test standards for making the comparison. The visual indicator may visualize or generate a signal of the sample and standards having a magnitude corresponding to the level of the marker present. The visual indicator may visualize or generate a signal for the first standard consistent with a first level of marker. The visual indicator may visualize a signal for the second standard consistent with a second level of marker.

For example, the visual indicator may visualize for the high standard a signal consistent with a level, such as the minimum level, of the biomarker (e.g., nitrated Y247) in a subject with the disease or disorder. The visual indicator may visualize for the low standard a signal consistent with a level, such as the maximum level, of the biomarker in a subject without the disease or disorder. The magnitude of the signal from the biological test sample generated by the visual indicator may be compared against the standards to determine the diagnosis.

Generating the visually detectable signal can be accomplished in several ways. Any visual indicator, including any dye, chromogen, substance, substrate, or solution capable of producing a qualitative indication or visually detectable change may be utilized and included with the kit or device. The generated signal may be visually detectable with or without special equipment. For example, the signal may be a color change, or the generation of a color change along a spectrum, that is visible without special equipment. In some embodiments, it is possible to detect changes in light absorbance visually, with non-specialized light detection equipment, or specialized equipment (e.g., Spectrophotometer). In some embodiments, the signal may be detected by measuring a change in a physical or chemical property of the substrate being tested based on the presence of a label, such as an enzyme label. Types of enzyme-labeled signals known to the art include: light absorbance, light emission, fluorescence, electrochemical signal, pH, etc.

The kits, devices, and assays can include instructions for use.

In some embodiments, the kit or device is used to assaying a biological sample, such as those discussed above.

EXAMPLES

Example 1

Y247 and Y425 are Nitration Sites on Human PKG-1α

Materials and Methods
Sources of Materials

Polyclonal anti-PKG-1α (goat), anti-Calponin-1 (rabbit), and monoclonal anti-Vimentin (Clone: 2Q1035) antibodies were from Santa Cruz Biotechnology (Santa Cruz, Calif.); Monoclonal anti-nitrotyrosine antibody (Clone: CC22.8C7.3) was from EMD Biosciences, Inc. (San Diego, Calif.); monoclonal anti-PCNA (Clone: PC 10) and polyclonal anti-SM22-α (goat) antibodies were from Abcam (Cambridge, Mass.); Monoclonal anti-β-actin (Clone: AC-15), and monoclonal anti-myosin heavy chain (MYH) (Clone: hSM-V) antibodies were from Sigma Life Sciences (St. Louis, Mo.); 3-morpholinosydnonimine Nethylcarbamide (SIN-1) was from Cayman Chemicals (Ann Arbor, Mich.); Bovine PKG full length recombinant protein (alpha1 isozyme) and a non-radioisotopic kit for measuring PKG activity were from Cyclex Co., Ltd. (Nagano, Japan); AlamarBlue was from AbD serotec (Raleigh, N.C.); [$^3$HcGMP] was from PerkinElmer (Waltham, Mass.); YASARA software was from YASARA Biosciences GmbH (Vienna, Austria); HEK-293T cells were a kind gift from Dr. John. D. Catravas.

Statistical Analysis

Statistical analysis was performed using GraphPad Prism version 4.01 (GraphPad Software, San Diego, Calif.). The mean±SEM was calculated in all experiments, and statistical significance determined either by the unpaired t-test (for 2 groups) or ANOVA (for >3 groups). For the ANOVA analyses, Newman-Kuels post-hoc testing was employed. A value of $p<0.05$ was considered significant.

Immunoprecipitation (IP) Analyses

Cells were homogenized in 3× weight/volume of IP buffer (25 mM Hepes, pH 7.5, 150 mM NaCl, 1% NP-40, 10 mM $MgCl_2$, 1 mM EDTA, 2% glycerol, supplemented with protease inhibitor). The homogenates were then centrifuged at 20,000 g at 4° C. for 20 min, the supernatant was collected, and the protein concentration was quantified by the Bio-Rad DC Protein Assay. To 1000 μg of total protein, 4 μg of antibody against PKG-1α was added; the volume was brought to 1 ml with IP buffer, and the mixture was incubated at 4° C. overnight. To precipitate the bound protein, 30 μl of protein G plus agarose suspension (EMD biosciences, Inc., San Diego, Calif.) was added, and the samples were incubated for 2 h at 4° C. To collect the bead-bound antibody, the samples were then centrifuged at 2000 g for 5 min at 4° C., the supernatant was removed, and the beads were washed 3× with 500 μl of IP buffer. To the samples, 30 μl of 2× Laemmli buffer was added, and the samples were boiled for 5 min and then resolved using 4-20% Tris-SDS-Hepes PAGE. The membrane was then probed for 3-nitrotyrosine (1:100 dilution), as described above. The IP efficiency was normalized by re-probing for PKG-1α (1:500).

In-Gel Digestion for Mass Spectrometry

HEK-293T cells were transfected with WT-PKG-1α cDNA for 48 h in high glucose DMEM media containing 10% FBS and 1% antibiotics and then serum starved (1% FBS) for 4 h. The cells were challenged with SIN-1 (500 μM) for 30 min, lysed, and then PKG-1α was purified using the immunoprecipitation technique, as mentioned above. The protein was resolved using 4-20% Tris-SDS-Hepes PAGE and visualized by Imperial Protein Stain (Thermo-Fisher). The band corresponding to PKG-1α (75 kD) was excised, destained, and subjected to overnight in-gel digestion with trypsin (25 ng/μl in 25 mM ammonium bicarbonate buffer, pH 7.8). The peptides were extracted with 0.1% TFA/75% acetonitrile and evaporated to near dryness.

MALDI-TOF Mass. Spectrometry

Peptide calibration standards and matrix CHCA were purchased from Applied Biosystems. All spectra were taken on an ABSciex 5800 MALDI-TOF Mass. Spectrometer in positive reflector mode (10 kV) with a matrix of CHCA. At least 1000 laser shots were averaged to get each spectrum. The masses were calibrated to known peptide standards. Aliquots (5 μl) of the PKG-1α tryptic digest were taken up into a C18 ZipTip (Millipore) that had been prepared, as per manufacturer's instructions. The bound peptides were desalted with two 5 μl washes of 0.1% TFA and then eluted with 2.5 μl of aqueous, acidic acetonitrile (75% CH3CN, 0.1% TFA). The eluate was mixed with 2.5 ul freshly prepared CHCA stock solution (20 mg/ml CHCA in aqueous acetonitrile, as above), and 1.5 μl portions of this mixture were spotted onto a MALDI sample plate for air drying.

Crude peptides (1.5 μl) were additionally mixed with CHCA (1.5 μl) and were spotted. The MS/MS of the 2209.04 m/z peak was done in positive reflector mode without CID. The MS and MS/MS spectra were analyzed in the Mascot Distiller software package.

Results

The association between nitration of PKG-1α and attenuation of kinase activity was shown previously (Aggarwal, S., et al., *Journal of Cellular Physiology* (2011)). However, the tyrosine residues susceptible to this posttranslational event are unknown. To identify nitration sites, HEK-293T cells were transfected with an expression plasmid containing a full length WT-PKG-1α cDNA. After 48 h the cells were exposed or not to the peroxynitrite generator, 3-morpholino-sydnonimine N-ethylcarbamide (SIN-1) (500 μM) for 30 min. The cells were lysed; PKG-1α was immunoprecipitated, and the protein was subjected to SDS-PAGE and Coomassie staining. The band corresponding to PKG-1α was excised, trypsinized, and mass spectrometry (MS) was performed on the extracted peptides.

MS analysis of the human 3-NT modified PKG-1α sequence, LADVLEETHYENGEYIIR (SEQ ID NO:2), corresponding to the peptide including the amino acids 233-250, and the sequence, QIMQGAHSDFIVRLYR (SEQ ID NO:3), corresponding to the peptide including the amino acids 411-426, demonstrated the nitration of Y247 and Y425 (Table 1).

TABLE 1

MS results showing Y247 and Y425 of PKG-1α are nitrated.

| Protein | MW | Protein PI | Pep Count | Protein score | Total ion score |
|---|---|---|---|---|---|
| cGMP dependent protein kinase type 1 alpha (*Homo Sapiens*) | 76943.2 | 5.74 | 17 | 266 | 250 |

| Peptide information | Calc. mass | Start Seq. | End Seq. | ±da | ±ppm |
|---|---|---|---|---|---|
| LADVLEETHYENGEYIIR[Nitro(Y)(15)] | 2209.04 | 233 | 250 | −0.964 | −432 |
| QIMQGAHSDFIVRLYR[Nitro(Y)(15), oxidation(M)(3)] | 1994.98 | 411 | 426 | −0.993 | −498 |

MS/MS was performed to verify the tyrosine nitration sites within PKG-1α. The peptide with m/z 2209.04 (parent peptide LADVLEETHYENGEYIIR (SEQ ID NO:2) with m/z 2164.04+45 Da of nitro group) was further fragmented and MS/MS data analyzed. The MS/MS spectrum of the 2209.04 m/z ion was obtained in positive reflector mode fitted with peptide 233-LADVLEETHYENGEXIIR-250 (SEQ ID NO:7) where "X" is 3-nitrotyrosine from the PKG-1α sequence. However, due to the low intensity of the peak corresponding to Y425, MS/MS could only confirm the nitration of Y247, indicating that Y425 is a poor nitration site.

Example 2

Nitration of Y247 Attenuates PKG-1α Activity

Materials and Methods

Generation of a Nitration Specific PKG-1α Polyclonal Antibody

The 3-NT Y247 PKG-1α specific antibody was raised against a synthetic peptide antigen ENGEXIIRQGARGDC (SEQ ID NO:5), where X represents 3-nitrotyrosine. The peptide was used to immunize rabbits. Tyrosine nitration-reactive rabbit antiserum was first purified by affinity chromatography. Further purification was carried out using immunodepletion by non-nitrated peptide ENGEYIIRQ-GARGDC resin chromatography, after which the resulting eluate was tested for antibody specificity by immunoblotting and immune-histochemistry with fluorescent staining Results To determine the role of tyrosine 247 and tyrosine 425 in mediating the nitration dependent inhibition of PKG-1α kinase activity, Y247F- and Y425F-PKG-1α mutants were generated and expressed in HEK-293T cells. HEK-293T cells were transiently transfected with expression plasmids containing WT-, Y247F-, or Y425F-PKG-1α for 48 h. Cells were also treated or not with SIN-1 (500 µM, 30 min). Protein extracts were immunoprecipitated using an antibody raised against PKG-1α and the level of nitrated PKG-1α determined by probing the membranes with an antiserum raised against 3-NT. The blots were then stripped and re-probed for PKG-1α to normalize for the efficiency of the immunoprecipitation.

Figure 1B:
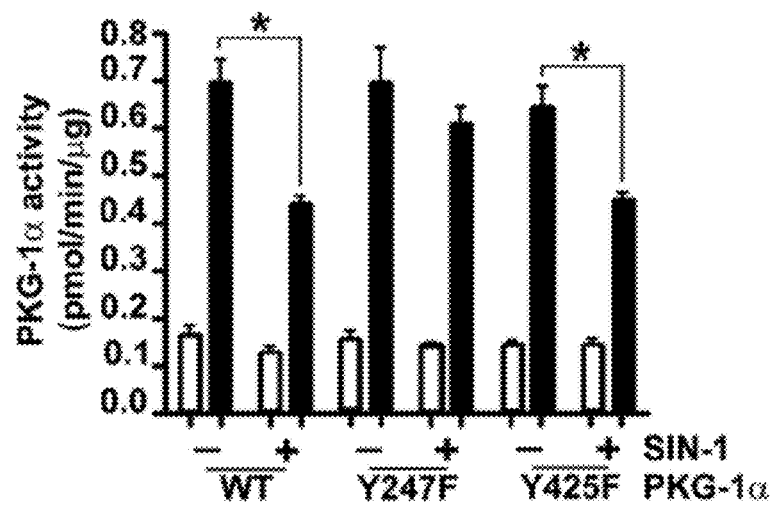

Immunoblot analysis verified increased expression of PKG-1α. The nitration of WT-PKG-1α was significantly increased in the presence of SIN-1 (FIG. 1A). However, there were no significant increases in the nitration levels of Y247F- or Y425F-PKG-1α in the presence of SIN-1 (FIG. 1A). Although SIN-1 did not alter cGMP-independent PKG activity (FIG. 1B, white bars), cGMP dependent PKG activity was attenuated in cells expressing WT- and Y425F-PKG-1α, but not in cells expressing Y247F-PKG-1α (FIG. 1B, black bars).

In conclusion, the moderate increase in the nitration levels of PKG-1α in the cells expressing either the Y247F or the Y425F mutant may be due to the nitration of the other tyrosine site. SIN-1 did not affect basal PKG-1α activity (without exogenous cGMP activation) (FIG. 1B). However, the cGMP-dependent increase in PKG-1α activity in the cells transfected with WT-, and Y425F-PKG-1α was attenuated in the presence of SIN-1, and the activity of the Y247F PKG-1α mutant was unaffected (FIG. 1B). Taken together, these results indicate that Y247 is involved in the nitration-mediated decrease in PKG-1α activity.

Example 3

Nitration of Y247 Attenuates PKG-1α Activity

Materials and Methods

Determination of PASMC Cell Growth

Pulmonary artery smooth muscle cells (PASMC) were grown on a 10 cm dish to 75% confluence, transfected with WT-PKG-1α or Y247F-PKG-1α cDNA using a Qiagen transfection kit, according to manufacturer's instructions, and incubated at 37° C. for 20 h. This method resulted in a ~20% transfection efficiency (not shown). The cells were then trypsinized, seeded onto a 6-well plate at a density of $2.5 \times 10^4$ cells per well, and grown for an additional 4 h in serum-free DMEM growth medium containing 1% FBS and antibiotics. The cells were then treated with or without SIN-1 (500 µM) and allowed to grow at 37° C. in the incubator for an additional 48 h. The cellular proliferation was evaluated by counting the cells with a hemacytometer (Cascade Biologicals™, Portland, Oreg.) after the trypsinization of the PASMC monolayers.

Analysis of PASMC Cellular Metabolism

This was determined via the alamarBlue assay (AbD Serotec, Oxford, UK). The assay is based on the reducing ability of metabolically active cells to convert the active reagent, resazurin, into a fluorescent and colorimetric indicator, resorufin. When added to cell cultures, the oxidized, resazurin enters the cytosol and is converted to the reduced, resorufin in the mitochondria by accepting electrons from NADH, NADPH, FADH2, FMNH2, as well as from the cytochromes. The non-toxic and cell permeable nature of alamarBlue permits the long-term exposure of cells. PASMC were grown on a 10 cm dish to 75% confluence, transfected with WT-PKG-1α or Y247F-PKG-1α cDNA, and incubated at 37° C. for 20 h. The cells were trypsinized and seeded onto a 24-well plate at a density of 20,000 cells per well and grown for an additional 4 h in serum and phenol free DMEM growth medium containing 1% FBS and antibiotics. The cells were then treated with or without SIN-1 (500 µM, 48 h) in the presence of 10% well volume of alamarBlue dye. The color change of the dye was determined at an excitation wavelength of 560 nm and an emission wavelength of 590 nm in a Fluoroskan Ascent plate reader. Cells exposed to 0.1% Triton X-100 were used as a negative control, while media containing alamarBlue dye autoclaved for 15 min was used to obtain the 100% reduced form of alamarBlue (positive control). Cellular metabolism was expressed as follows:

$$\% \text{ reduction of } alamarBlue = \frac{\text{Sample value} - \text{Negative control}}{\text{Position control} - \text{Negative control}} \times 100\%$$

Results

Figure 2A:
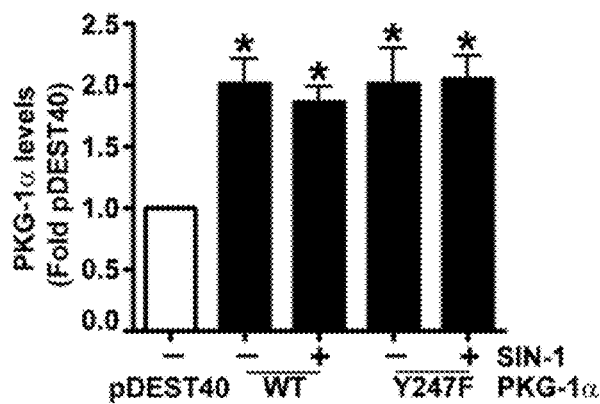
FIGS. 2A-2D are histograms showing variations in PKG-1α levels, (Fold pDEST40) (FIG. 2A); PKG activity (pmol/min/μg) (FIG. 2B); Cell count (Fold change day 0) (FIG. 2C); and Percentage of reduction of alamarBlue (FIG. 2D), respectively, for control plasmid (pDEST40, white bar), wild type PKG-1α (WT) and Y247F PKG-1α (Y247F), with or without SIN-1, respectively. Data are mean±SEM, n=4, *p<0.05 vs. pDEST40, † p<0.05 vs. WT-PKG-1α, ‡ p<0.05 vs. WT-PKG-1α+SIN-1.
Figure 2B:
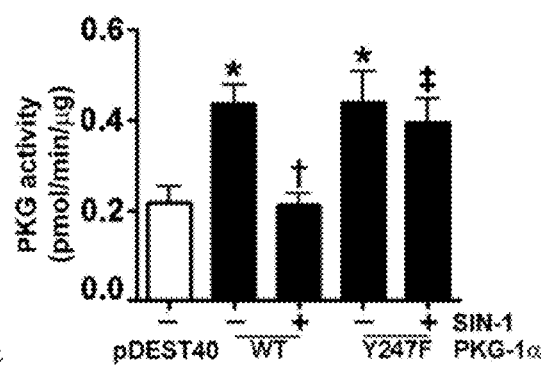

Past studies have demonstrated that the expression of PKG-1 results in decreased proliferation (Kawashima, S., et al., *Arteriosclerosis, Thrombosis, and Vascular Biology* 21, 201-207 (2001); Rudic, R. D., et al., *The Journal of Clinical Investigation* 101, 731-736 (1998)) and acquisition of a contractile phenotype in vascular SMC (VSMC) (Pilz, R. B., et al., *Front Biosci* 10, 1239-1268 (2005)). Therefore, the effect of these events were investigated in PASMC transiently transfected with expression plasmids containing WT- and Y247F-PKG-1α. The effect of nitration on pulmonary arterial smooth muscle cell (PASMC) growth and metabolism was determined. PASMC were transiently transfected with expression plasmids containing WT-PKG-1α, Y247F-PKG-1α or pDEST40 (as a control) for 20 h. Cells were then exposed or not to SIN-1 (500 µM, 48 h) and the effect on PKG protein levels (FIG. 2A) and activity determined (FIG. 2B).

Whether SIN-1 attenuated PKG kinase activity in cells transfected with WTPKG-1α but not in cells expressing Y247F-PKG-1α was confirmed. The effect on PASMC proliferation and metabolic activity was determined. SIN-1 had no effect on PKG-1α protein levels (FIG. 2A). SIN-1 attenuated the cGMP dependent increase in PKG activity in the cells transfected with WT-PKG-1α, but not those expressing the Y247F PKG-1α mutant (FIG. 2B). The effect of SIN-1 on cellular proliferation (FIG. 2C) and cellular metabolic activity (FIG. 2D) were also determined. PASMC expressing either WT- or Y247F-PKG-1α were less proliferative and metabolically active than the pDEST40 transfected control cells. SIN-1 exposure stimulated proliferation and metabolism in WT-, but not Y247F-PKG-1α transfected PASMC. The transfection efficiency in the PASMC was approximately 20%.

Figure 2C:
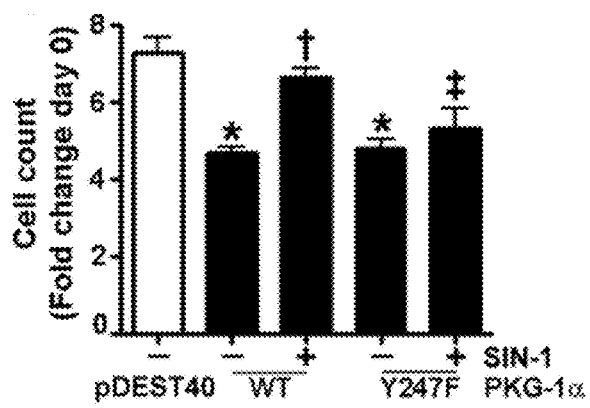
Figure 2D:
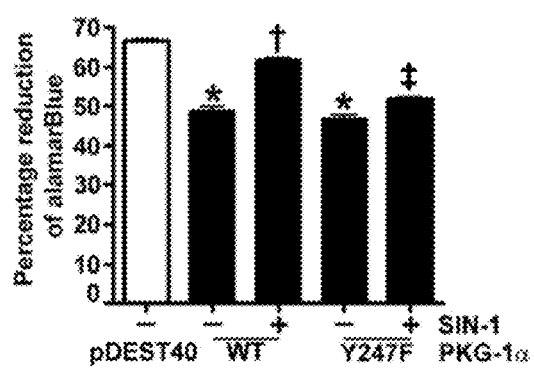

In conclusion, the results demonstrated that PASMC transfected with either WT- or Y247F-PKG-1α had lower cell counts and metabolic activity compared to those transfected with the parental vector, pDEST40. SIN-1 exposure induced proliferation and metabolic activity in the PASMC expressing WT-PKG-1α but not in the cells transfected with the Y247F-PKG-1α mutant (FIGS. 2C and 2D).

Example 4

Nitration Alters the Phenotype of Pulmonary Arterial Smooth Muscle Cells

Materials and Methods

Western Blot Analysis

Cells were prepared as previously described (Sud, N., et al., *American Journal of Physiology* 293, L1444-1453 (2007); Sharma, S., et al., *American Journal of Physiology* 294, L46-56 (2008)). Briefly, the cellular protein extracts were prepared by homogenizing the cells in lysis buffer (50 mM Tris-HCl, pH 7.6, 0.5% Triton X-100, and 20% glycerol) containing Halt protease inhibitor cocktail (Pierce, Rockford, Ill.). The extracts were then clarified by centrifugation (20,000 g for 20 min at 4° C.). The supernatant fractions were assayed for protein concentration using the Bio-Rad DC Protein Assay (Bio-Rad Laboratories, Hercules, Calif.) and used for Western blot analysis. Similarly, peripheral lung tissue from the control lambs and the lambs with pulmonary hypertension secondary to increased pulmonary blood flow (shunt) was prepared as described earlier (Aggarwal, S., et al., *Journal of Cellular Physiology* (2011)). Cell extracts (25 µg) were resolved using 4-20% Tris-SDS-Hepes PAGE, electrophoretically transferred to Immuno-Blot™ PVDF membrane (Bio-Rad Laboratories, Hercules, Calif.), and then blocked with 5% nonfat dry milk in Tris buffered saline. The membranes were then probed with antibodies against PKG-1α (1:500 dilution), anti-nitrotyrosine 247-PKG-1α (1:500), Calponin-1 (1:500 dilution), Vimentin (1:500 dilution), or MYH (1:500 dilution). Reactive bands were visualized using chemi-luminescence (Pierce Laboratories, Rockford, Ill.) on a Kodak 440CF image station. The band intensity was quantified using Kodak 1D image processing software. The protein expression was normalized by re-probing with anti β-actin (1:2000).

Immunocytochemistry

Semi-confluent PASMC grown on a coverslip in a 6-well plate were transfected with a mammalian expression plasmid containing either a wild-type (WT)- or Y247F-PKG-1α cDNA. After 20 h, the cells were serum starved (1% FBS) for 4 h then exposed or not to SIN-1 (500 µM) for 48 h. The cells were washed with PBS, methanol fixed (5 min), and permeabilized in 0.1% PBS-Tween (20 min). The cells were then washed 3× with PBS and blocked for non-specific protein-protein interactions with 1% BSA in PBS (1 h). The antibodies, smooth muscle (SM) 22-α (5 µg/ml) or proliferating cell nuclear antigen (PCNA) (1 µg/ml) diluted in 1% BSA in PBS, were added and incubated overnight at 4° C. The cells were again washed 3× with PBS and incubated in secondary antibody (green): Alexa Fluor 488 goat anti-mouse IgG (H+L) (1/1000 dilution) for PCNA or Alexa Fluor 488 donkey anti-goat IgG (H+L) (1/1000 dilution) for SM22-α for 1 h in the dark. DAPI was used to stain the cell nuclei (blue) at a concentration of 0.5 µg/ml for 3 min. The cells were rinsed 3× with PBS, and the coverslips were mounted on the slides with ProLong Gold Antifade and analyzed with the use of a Nikon Eclipse TE 300 inverted fluorescent microscope with a 60× oil objective and a Hamamatsu digital camera.

Results

To assess the effect of nitration on pulmonary arterial smooth muscle cell (PASMC) phenotype, PASMC were transiently transfected with expression plasmids containing WT-PKG-1α, Y247F-PKG-1α, or PDEST40 (as a control) for 20 h. Cells were then exposed or not to SIN-1 (500 µM, 48 h) and the effect on synthetic and contractile markers determined. The levels of myosin heavy chain (MYH, FIG. 3A), Calponin-1 (FIG. 3B), and Vimentin (FIG. 3C) were determined. The blots were then stripped and re-probed for β-actin to normalize for protein loading. PASMC were also subjected to immunohistochemistry using antibodies to SM22-α (5 µg/ml) and PCNA (1 µg/ml). Relevant secondary antibodies linked to Alexa Fluor 488 (green) were then applied. DAPI was also used to stain (blue) the cell nuclei.

In addition to its role in mediating the vasodilator effects of NO, PKG contributes to the maintenance of a contractile-like phenotype in SMC, and the suppression of PKG expression/activity in vitro induces a more synthetic, dedifferentiated phenotype (Lincoln, T., et al., *Acta Physiologica Scandinavica* 164, 507-515 (1998)). The transition of VSMC from a contractile to a proliferative phenotype appears to be an early event in various pathologies, such as pulmonary hypertension, atherosclerosis, and restenosis (Negash, S., et al., *American Journal of Physiology* 297, H304-312 (2009); Acampora, K. B., et al., *Annals of Vascular Surgery* 24, 116-126; Dusserre, E., et al., *Biochimica Et Biophysica Acta* 1212, 235-244 (1994)), and is associated with increased oxidative and nitrosative stress (Klemm, D. J., et al., *Journal of Cardiovascular Pharmacology* 58, 181-191; Madamanchi, N. R., et al., *Arteriosclerosis, Thrombosis, and Vascular Biology* 25, 950-956 (2005); Wang, J. N., et al., *Free Radical Biology & Medicine* 52, 173-181). Although the precise mechanisms by which oxidative stress induces a proliferative phenotype are still unresolved, reactive oxygen and nitrogen species (ROS and RNS) have been shown to attenuate PKG-1α signaling in both experimental and human forms of pulmonary hypertension as a result of diminished catalytic activity (Aggarwal, S., et al., *Journal of Cellular Physiology* (2011); Zhao, et al., *The Journal of Clinical Investigation* 119, 2009-2018 (2009)) or protein expression (Negash, et al., *American Journal of Physiology* 293, L1012-1020 (2007)). Protein nitration is emerging as an important posttranslational event responsible for attenuating PKG-1α activity. ROS and RNS levels are increased in pulmonary hypertensive mice (Nisbet, R. E., et al., *American Journal of Respiratory Cell and Molecular Biology* 40, 601-609 (2009)), lambs (Aggarwal, S., et al., *Journal of Cellular Physiology* (2011)), and humans (Zhao, et al., *The Journal of Clinical Investigation* 119, 2009-2018 (2009) and the increase in oxidative and nitrosative stress is implicated in both vasoconstriction (Broughton, B. R., et al., *American Journal of Physiology* 298, L232-242) and vascular remodeling (Nozik-Grayck, E., et al., *Advances in Experimental Medicine and Biology* 618, 101-112 (2007)).

Studies have identified nitration and the ensuing attenuation of PKG-1α activity in the lungs of lambs with pulmonary hypertension secondary to increased pulmonary blood flow and in lambs with rebound pulmonary hypertension associated with the acute withdrawal of inhaled NO therapy (Aggarwal, S., et al., *Journal of Cellular Physiology* (2011)). In addition, the nitration and subsequent attenuation of PKG activity in the right ventricle (RV) appears to be responsible for the deterioration of RV function in a mouse model of PH induced by chronic hypoxia (Cruz, J. A., et al., *American Journal of Physiology* 302, H2518-2527). While the increase in protein nitration associated with hypoxia reduces PKG activity through changes at the transcriptional and post-translational levels (Negash, et al., *American Journal of Physiology* 293, L1012-1020 (2007)). The clinical relevance of PKG nitration has also been shown by the observation that patients with idiopathic pulmonary arterial hypertension have increased PKG nitration in their lungs with no noticeable alteration in PKG protein levels (Zhao, et al., *The Journal of Clinical Investigation* 119, 2009-2018 (2009)). Thus, the accumulated data indicate that the nitration-dependent impairment of PKG activity is an important event in the development of vascular dysfunction in pulmonary hypertension.

Figure 3A:
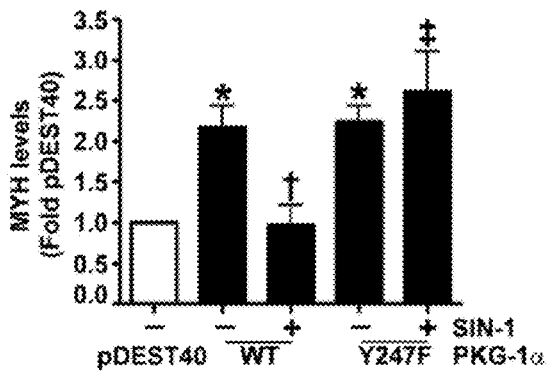
FIGS. 3A-3E are histograms showing MYH levels (Fold pDEST40) (FIG. 3A); Calponin-1 levels (FIG. 3B); Vimentin levels (Fold pDEST40) (FIG. 3C); % Filamentous SM22-α positive PASMC (FIG. 3D); and % PCNA positive nuclei (FIG. 3E), respectively, for control plasmid (pDEST40, white bar), wild type PKG-1α (WT) and Y247F PKG-1α (Y247F), with or without SIN-1, respectively. Data are mean±SEM, n=4-7, *p<0.05 vs. pDEST40, † p<0.05 vs. WT-PKG-1α, ‡ p<0.05 vs. WT-PKG-1α+SIN-1.
Figure 3B:
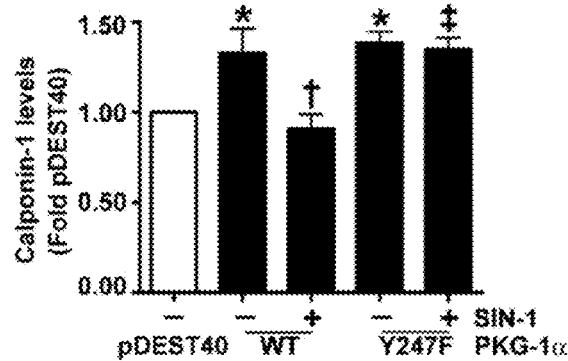
Figure 3C:
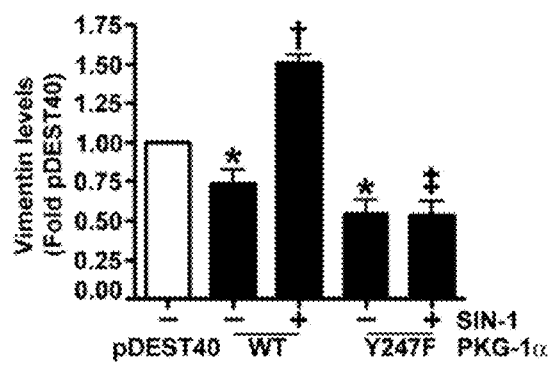
Figure 3D:
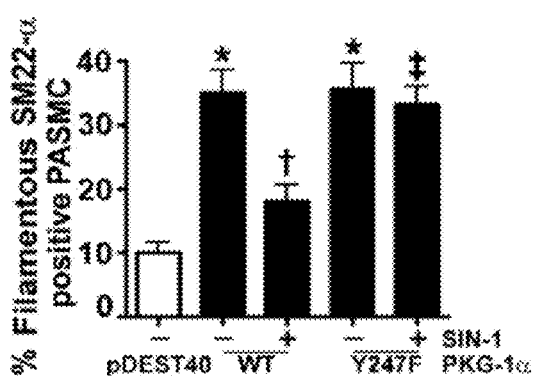

Therefore, the effect of Y247 nitration was examined in vitro and in vivo. Immunoblot analysis demonstrated that PASMC transfected with WT and Y247F-PKG-1α exhibited a contractile phenotype, as illustrated by the increased levels of the contractile markers: MYH and Calponin-1 (FIGS. 3A and 3B) and decreased levels of the proliferative marker, Vimentin (FIG. 3C). However, when exposed to SIN-1, WT-PKG-1α expressing PASMC acquired a more proliferative phenotype compared to the cells transfected with the Y247F-PKG-1α mutant (FIGS. 3A-C). The immunocytochemistry analysis also found that the PASMC transfected with the WT- and the Y247F-PKG-1α were spindle shaped and had increased expression of contractile phenotype marker, SM22-α, bound to actin stress fibers (FIG. 3D). In contrast, the nuclear levels of the proliferative marker protein, PCNA, were decreased (FIG. 3E) in these cells. SIN-1 treatment attenuated SM-22α expression and increased PCNA staining in the WT- but not in the Y247F-PKG-α expressing cells indicating that the Y247F-PKG-α mutant is resistant to phenotype modulation by nitrosative stress.

Figure 3E:
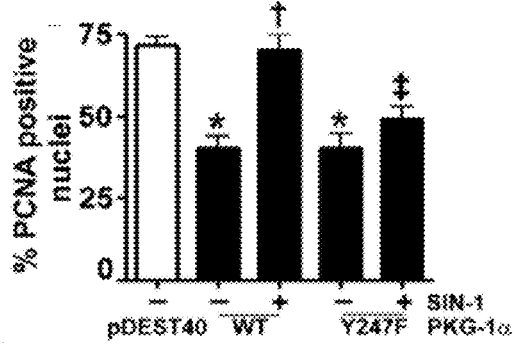

In conclusion, under basal conditions, PASMC transfected with the WT- and the Y247F-PKG-1α exhibited increased expression of the contractile markers, MYH and Calponin-1 and decreased expression of the proliferative marker, Vimentin indicative of a contractile phenotype. SIN-1 decreased the expression of the contractile markers, MYH and Calponin-1 and increased the expression of the proliferative marker, Vimentin in the WT-PKG-1α transfected cells, indicative of a proliferative phenotype. The Y247F PKG-1α expressing cells were resistant to this phenotypic conversion. PASMC expressing WT- or Y247FPKG-1α acquired a contractile phenotype with the increased filamentous binding of the SM22-α protein on the actin stress fibers (FIG. 3D). The nuclear localization of PCNA was also reduced in these cells (FIG. 3E). However, when PASMC were treated with SIN-1, the WT PKG-1α expressing cells exhibited decreased filamentous SM22-α expression and increased nuclear staining of PCNA, while the Y247F-PKG-1α expressing cells were unaffected.

Example 5

Y247-PKG-1α Nitration Occurs In Vitro and In Vivo

Materials and Methods

Immunohistochemistry and Immunofluorescence Microscopy

Normal and pulmonary hypertensive (PH) human lung tissue paraffin sections (5 μm) were mounted on slides and placed in a 55° C. oven for ten minutes, deparaffinized in xylene (3×, 5 min), then hydrated using an alcohol series— 100%, 95%, 70% alcohol (each 3×, 5 min) and finally rinsed in water. The sections were processed for antigen retrieval by boiling the slides in 10 mM Citrate Buffer (pH 6.0). The slides were then cooled at room temperature for 20 minutes, washed in PBS and blocked in 10% normal serum overnight at 4° C. Immunofluorescence was then performed on serial sections from each group using goat anti-PKG-1α, rabbit anti-3-NT-Y247-PKG-1α, and mouse anti-caldesmon antibodies (Sigma). The sections were incubated with primary antibodies for 1 h at room temperature and washed (3×, 5 min) with PBS. Subsequently, sections were double stained either with Alexa Fluor® 546 anti-goat or anti-rabbit secondary antibodies (Molecular Probes, Inc.) and Alexa Fluor® 488 anti-mouse secondary antibodies. Sections were washed several times in PBS, mounted on the cover slip in anti-fading aqueous mounting medium. The fluorescent-stained sections were then analyzed using the appropriate excitation and emission wavelengths by performing confocal microscopy using a computer-based DeltaVision imaging system (Applied Precision Inc.).

Lamb Model of Pulmonary Hypertension

The surgical preparation to introduce fetal aorta-pulmonary shunt was carried out as previously described (Reddy, V. M., et al., *Circulation* 92, 606-613 (1995)). All protocols and procedures were approved by the Committee on Animal Research at the University of California, San Francisco and the Institutional Animal Care and Use Committee at Georgia Regents University.

Human Specimens

Four bilateral lung explants were selected from human patients who underwent lung transplantation because of Eisenmenger's syndrome ("associated pulmonary arterial hypertension", NYHA IV). All lung specimens showed prominent plexiform vasculopathy (age at transplantation: 36.5±11.04 years; female:male ratio—4:1). All the specimens were inflated with formalin via the main bronchi and were formalin-fixed overnight before being extensively sampled and paraffin-embedded (FFPE). Subsequently, they were histologically evaluated, graded according to the Heath-Edwards classification (all grade 5), and correlated with clinical data to confirm the (histopathologic) diagnosis. The FFPE samples were retrieved from the archives of the Institute of Pathology of Hannover Medical School and were handled anonymously, following the requirements of the local ethics committee (Jonigk, D., et al., *The American Journal of Pathology* 179, 167-179).

Cell Culture

Primary cultures of pulmonary artery smooth muscle cells (PASMC) from 4-week old lambs were isolated by the explant technique, as previously described (Wedgwood, S., et al., *Circulation Research* 89, 357-364 (2001)). Briefly, a segment of the main pulmonary artery from a 4-week old lamb was excised and placed in a sterile 10 cm dish containing DMEM supplemented with 1 gm/1 glucose. The segment was stripped of adventitia with a sterile forceps. The main pulmonary artery segment was then cut longitudinally to open the vessel, and the endothelial layer was removed by gentle rubbing with a cell scraper. The vessel was then cut into 2 mm segments, inverted, and placed on a collagen coated 35 mm tissue culture dish. DMEM (~50 μl) containing 10% FBS (Hyclone), antibiotics, and antimycotics (MediaTech) was then added to each segment, and the cells were grown overnight at 37° C. in a humidified atmosphere with 5% $CO_2$ and 95% air. The next day an additional 2 ml of medium was added. The growth medium was subsequently changed every 2 days. When SMC islands were observed under the microscope, the tissue segment was removed, and the individual cell islands were sub-cloned using cloning rings. The identity of PASMC was confirmed by immunostaining (>99% positive) with SMC actin, caldesmon, and calponin. All cultures for subsequent experiments were maintained in DMEM supplemented with 10% FBS, 1% antibiotics, and antimycotics at 37° C. in a humidified atmosphere with 5% $CO_2$ and 95% air. All experiments were conducted in cells between passages 5 and 15.

Results

PASMC were transiently transfected with expression plasmids containing WT- or Y247FPKG-1α for 48 h. Cells were then treated or not with SIN-1 (500 µM, 30 min). An anti-Y247-PKG-1α antibody was developed to directly analyze the nitration of Y247 in cells and tissues. Protein extracts were immunoblotted and probed with antibody raised against 3-NT-Y247-PKG-1α. The blots were then stripped and re-probed for total β-actin to normalize loading. Immunohistochemical analysis was performed on lung sections prepared from humans with pulmonary hypertension (PH). The antibodies used were goat anti-PKG-1α (red), 3-NT-Y247-PKG-1α (red), and anti-caldesmon (green). The fluorescent-stained sections were analyzed using confocal microscopy.

Figure 4A:
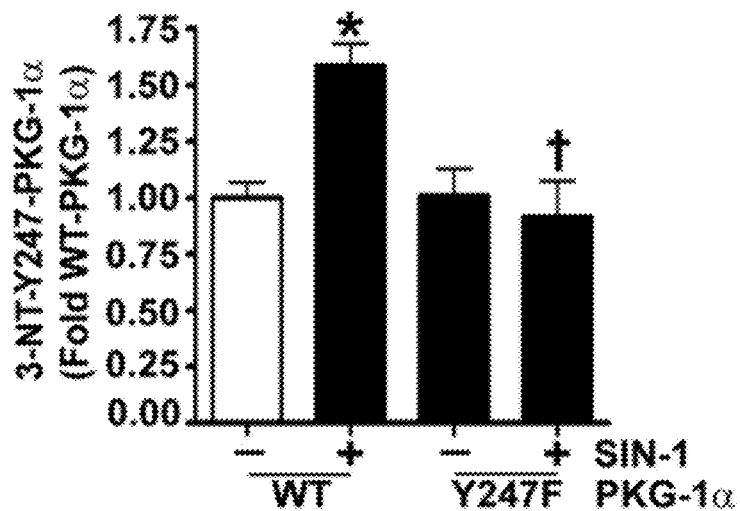
FIGS. 4A-4C are histograms.
Figure 4B:
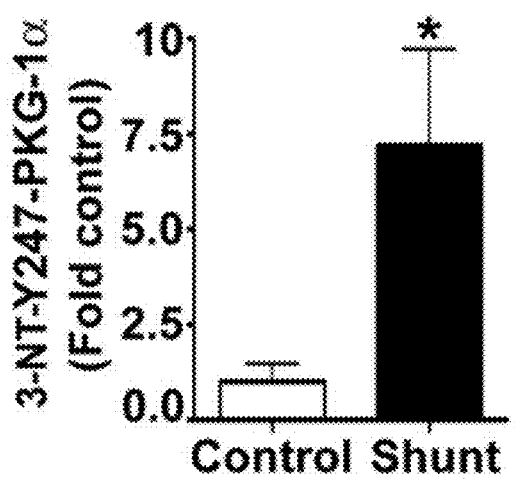
Figure 4C:
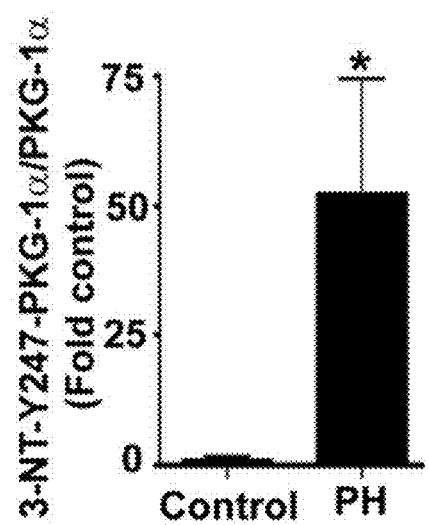

WT-PKG-1α nitration was significantly increased in the presence of SIN-1 in PASMC (FIG. 4A). However, there were no significant increases in the nitration levels of 3-NT-Y247-PKG-1α in the presence of SIN-1 (FIG. 4A). The 3-NT-Y247-PKG-1α antibody also detected higher PKG-1α nitration levels in peripheral lung tissues of lambs with pulmonary hypertension secondary to increased pulmonary blood flow (FIG. 4B). The 3-NT-Y247-PKG-1α antibody identified significantly higher levels of nitrated PKG-1α in the lungs of patients with PH and this was predominant in the smooth muscle layer (FIG. 4C).

In conclusion, using immunoblot analysis, anti-Y247-PKG-1α antibody detected higher levels of nitrated PKG-1α in PASMC transfected with WT-PKG-1α compared to Y247F-PKG-1α with SIN-1 treatment (FIG. 4A). This antibody also detected high levels of Y247 nitration in the peripheral lung tissue of lambs with pulmonary hypertension secondary to increased pulmonary blood flow (FIG. 4B) confirming the results of earlier studies (Aggarwal, S., et al., *Journal of Cellular Physiology* (2011)). Further, immunohistochemical analysis identified greater signal in the pulmonary vessels from patients suffering from idiopathic pulmonary hypertension (Zhao, et al., *The Journal of Clinical Investigation* 119, 2009-2018 (2009)) compared to controls (FIG. 4C). Together these data indicate that the nitration of Y247 is an important mechanism by which nitrative stress impairs PKG-1α activity both in vitro and in vivo.

Example 6

Generation of a Homology Model of Human PKG-1α

Materials and Methods

Generation of the Homology Model

The YASARA Structure version has a complete homology modeling module that performs automatically all the steps from amino acid sequence (input) to a refined high resolution model (output). The PKG-1α homology model was obtained using the following protocol. A PSI-BLAST (Altschul, S. F., et al., *Nucleic Acids Research* 25, 3389-3402 (1997)) integrated in YASARA was used to identify the closest templates in the PDB. As a template for the 3-dimensional structure for the PKG-1α homology model, the regulatory (PDB 1NE4) and catalytic (PDB 2CPK) domains of PKA were used because PKA shares significant structural and functional similarities to PKG-1α. BLAST was used to retrieve homologous sequences, create a multiple sequence alignment, and enter the sequences into a 'Discrimination of Secondary Structure Class (DSC)' prediction algorithm (King, R. D., et al., *Protein Sci* 5, 2298-2310 (1996)).

The side-chains were added and optimized in the next step, and all of the newly modeled parts were subjected to a combined steepest descent and underwent simulated annealing minimization. The backbone atoms of the aligned residues were kept fixed to avoid potential damage. Finally, an unrestrained, simulated, annealing minimization with water was performed on the entire model. The resultant individual homology models of the PKG-1α regulatory domain and the catalytic domain were combined together to form a single PDB sequence. This sequence was used as a template sequence for generating a complete homology model of PKG-1α using the procedure described above resulting in a PKG-1α structure containing two cGMP binding sites: A and B as well as an ATP binding site represented by β-sheets.

Subsequently, docking of two cGMP molecules and one ATP molecule to their respective binding sites was performed. A simulation cell was placed around each ligand binding site on the PKG-1α homology model to focus the docking of the specific ligand on the known specific binding regions. The AutoDock program, developed at the Scripps Research Institute, was used to dock the ligands. A $NO_2$ group was introduced into the protein model on the ortho carbon of the phenolic ring of the Y247 residue. The structure was minimized, and the hydrogen bonding energy (kJ/mol) and distance [Angstrom (Å)] between the cGMP molecule and the cGMP binding site B of PKG-1α were analyzed in the presence or absence of the $NO_2$ group again using YASARA.

Results

To further understand the molecular mechanism(s) by which nitration of Y247 impairs PKG-1α activity, a homology model of full length PKG-1α protein was developed. Since a complete X-ray structure for PKG-1α is unavailable in the protein data bank (PDB), the structure's homology modeling module of YASARA (Yet Another Scientific Artificial Reality Application) were used (Venselaar, H., et al., *Eur. Biophys J* 39, 551-563) to build a high resolution model of PKG-1α from its amino acid sequence. Due to the labile structure of PKG-1 only the dimerization region in the regulatory domain in PKG-1β (Casteel, D. E., et al., *The Journal of Biological Chemistry* 285, 32684-32688), and the regulatory domains of PKG-1α (amino acids 78-355) (Osborne, B. W., et al., *Structure* 19, 1317-1327) and PKG-1β (amino acids 92-227) (Kim, J. J., et al., *PloS One* 6, e18413) have been crystallized and characterized. Therefore, the known crystal structures of the regulatory (PDB 1NE4) and the catalytic (PDB 2CPK) domains of PKA were used as templates to build a homology model. The YASARA homology modeling software was used to build a homology model of the PKG-1α regulatory domain using the known crystal structure of the PKA regulatory domain (PDB 1NE4), as a template. The known crystal structure of the catalytic domain of PKA (PDB 2CPK) was used to construct the corresponding homology model of the catalytic domain of PKG-1α. Using the homology models of these two domains of PKG-1α, a complete 3-dimensional model of the protein was generated. The AutoDock program was then used to dock two cGMP molecules to the cGMP binding sites: A and B and an ATP molecule to the ATP binding site.

Figure 5A:
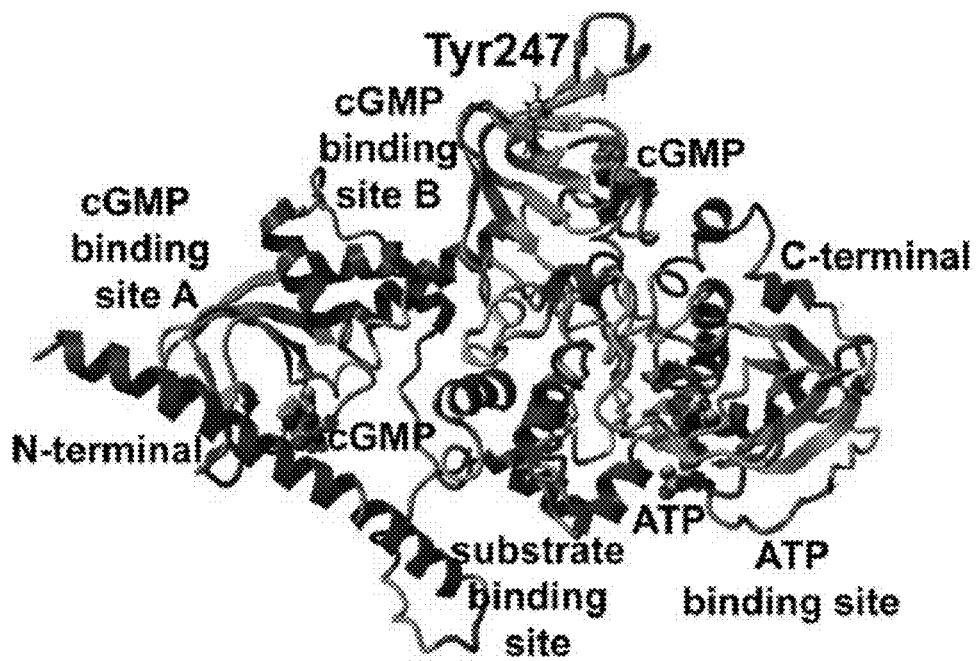
FIGS. 5A-5D are cartoon representations of the molecular structure of human PKG-1α regulatory domain, based upon the crystal structures of the catalytic domain of PKA (PDB 2CPK) and the PKG-1α PKA regulatory domain (PDB 1NE4).
Figure 5B:
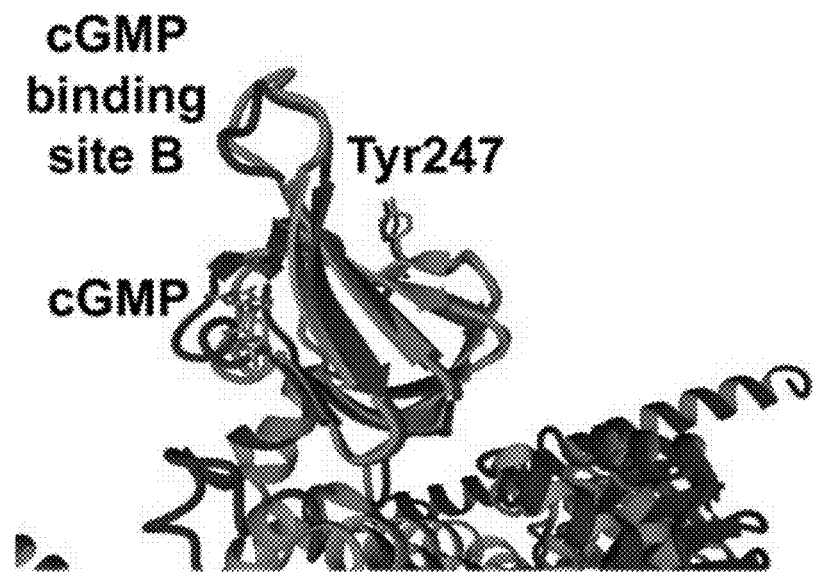
Figures 5C, 5D:
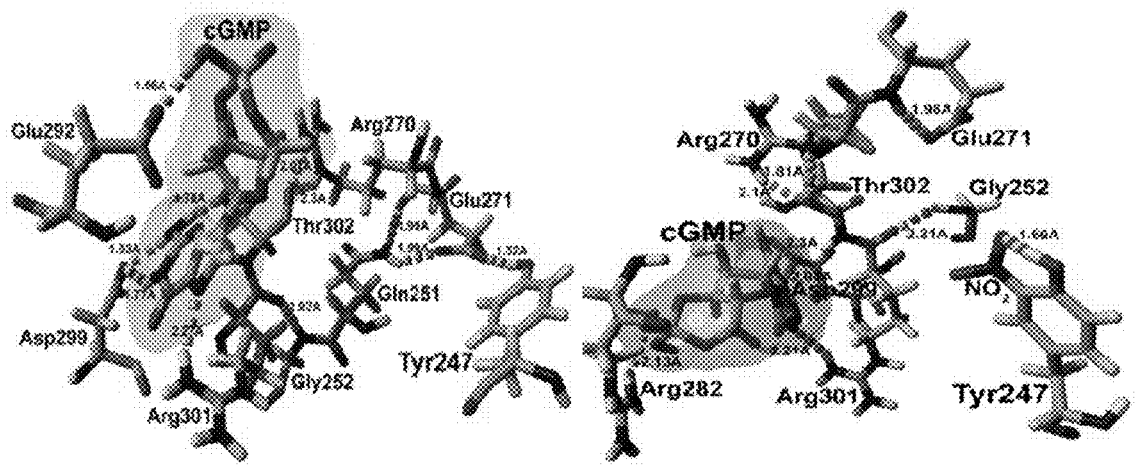

The analysis of the resulting 3-dimensional PKG-1α structure indicated that Y247 shares a close proximity to the cGMP binding site B (FIG. 5A). Further, the superimposition and comparison of the recently crystallized structure of PKG-1α (Osborne, B. W., et al., *Structure* 19, 1317-1327)) and the homology model demonstrated high similarity within the cGMP binding site B, even though this crystal structure was not used to build the homology model (FIG. 5B). Further, molecular dynamic simulations in the model after the addition of a $NO_2$ group to the Y247 predicted the loss of a hydrogen bond between the cGMP molecule and threonine 302 of PKG-1α, the residue responsible for nucleotide specificity of cGMP binding site B (FIG. 5C). The YASARA homology modeling software was used to predict the affinity of cGMP for the cGMP binding site B in the PKG-1α homology model under control (FIG. 5C) and nitrative stress conditions (FIG. 5D). The $NO_2$ group was predicted to displace the hydrogen bond between cGMP and glutamate 292 and form a new hydrogen bond between cGMP and arginine 282 of PKG-1α (FIG. 5D). The addition of a $NO_2$ group to Y247 is predicted to decrease the total hydrogen bonding energy between cGMP and PKG-1α from 91.93 kJ/mol to 54.02 kJ/mol (FIGS. 5C-D).

In conclusion, the nitration of Y247 should result in a net loss of 1 hydrogen bond between cGMP and PKG-1α and an increase in bond lengths with a predicted net decrease in total hydrogen bonding energy between cGMP and PKG-1α from 91.93 kJ/mol to 54.02 kJ/mol (FIGS. 5C-D).

Example 7

Nitrative Stress Affects cGMP Binding and Dissociation Characteristics of PKG-1α

Materials and Methods
Measurement of PKG Catalytic Activity

Total PKG activity was determined using a non-radioactive immunoassay in cell lysates, according to the manufacturer's directions. Briefly, protein samples were diluted in kinase reaction buffer containing $Mg^{2+}$ and ATP (125 μM) in the presence or absence of 8-Br cGMP (10 μM) and incubated in a 96 well plate pre-coated with a PKG substrate containing threonine residues phosphorylated by PKG.

After incubation for 30 min at 30° C. to allow the phosphorylation of the bound substrate, an HRP conjugated anti-phosphothreonine specific antibody was added to convert a chromogenic substrate to a colorimetric substrate that was subsequently read spectrophotometrically at 450 nm. The change in absorbance reflected the relative activity of PKG in the sample. The results were reported as pmols of phosphate incorporated into the GST-G substrate fusion protein by active PKG in the sample in the presence or absence of cGMP (10 μM) per minute at 30° C. per μg of protein (pmol/min/μg). These results were extrapolated by comparing the spectrophotometrical values of the samples to the known activity (pmol/min) of recombinant PKG-1α protein, as a positive control. The kinetic constants were determined using nonlinear regression (curve fit) analysis (GraphPad Prism Software Inc.).

To determine the Michaelis-Menten constant (Km) for cGMP, the kinase assay was performed, as mentioned above; however, the cGMP concentration was titrated from 0-10 μM, while the ATP concentration remained constant at 125 μM.

[$^3$H]cGMP Binding Assay

HEK-293T cells were transiently transfected with either the WT-PKG-1α or the Y247FPKG-1α cDNA using Effectene transfection reagent (Qiagen), according to the manufacturer's instructions. Briefly, the cells were split the day before the transfection to low cell densities (25%) and were transfected 24 h later. After 48 h of transfection, the cells were incubated in DMEM serum free media containing 1% FBS and antibiotics for 4 h and then treated with or without SIN-1 (500 μM), for 30 min. This method produced an approximate 70% transfection efficiency of HEK-293T cells, as measured using green fluorescent protein vectors.

In order to purify PKG-1α, three 10 cm dishes of cells were transfected for each purification group. After treatment with SIN-1, the cells were placed on ice, the media was aspirated, and replaced with 10 ml of ice cold PBS. All subsequent steps were performed on ice. The cells were scraped and clarified by centrifugation. The cell pellets were resuspended (1 ml/10 cm dish) in lysis buffer (50 mM Tris-HCl, pH 7.0, 1 mM EDTA, 1% Nonidet P-40, 150 nM NaCl) containing phosphatase and protease inhibitor cocktails for 20 min at 4° C. followed by clarification by centrifugation at 20,000 g for 20 min.

The batches of supernatant were pooled, and 2 μg of anti-PKG-1α antibody per mg of protein were added to the extract and rocked at 4° C. After 4 h of incubation, protein G PLUS-agarose beads (10 μl/mg protein) were added and incubated overnight with nutation at 4° C. The beads were washed three times in lysis buffer. The PKG-1α attached to the beads was then eluted by the resuspension in 100 μl of PBS containing 5 μg of PKG-1α peptide (Santa Cruz Biotechnology) per μg of antibody. After 15 min of agitation at 4° C., the beads were pelleted by centrifugation, and the supernatant containing the PKG-1α protein was collected, quantified using Bradford reagent, and stored at −80° C.

To assay the binding of cGMP to WT- and Y247F-PKG-1α the enzymes were saturated with cGMP by incubating 50 μl aliquots of the diluted PKG constructs for 60 min at room temperature with 50 μl of [$^3$H]cGMP and 150 μl of cGMP-binding assay mixture (25 mM $K_2HPO_4$, 25 mM $KH_2PO_4$, 1 mM EDTA, pH 6.8, 2M NaCl, 200 μM 3-isobutyl-1-methylxanthine). The final cGMP concentration varied from 0 to 200 nM, and the final concentration of enzyme was 100 ng. After incubation, 2 ml of cold aqueous saturated $(NH_4)_2SO_4$ was added to each sample. The samples were then filtered onto 0.45 μm pore nitrocellulose paper (Millipore) that had been pre-moistened with saturated $(NH_4)_2SO_4$ and were then rinsed three times with 2 ml of cold saturated $(NH_4)_2SO_4$. The papers were dried and shaken in vials containing 1.5 ml 2% SDS. Aqueous scintillant (10 ml) was added; the vials were shaken again and then counted in a liquid scintillation counter. The dissociation constant (Kd) values were determined using GraphPad Prism graphics.

[$^3$H]cGMP Dissociation/Exchange assay

WT- and Y247F-PKG-1α were immunopurified, as described above then incubated for 60 min at room temperature with 3 ml of cGMP-binding assay mixture containing 3 μM [$^3$H]cGMP. This incubation time and dose has been previously experimentally determined to be adequate for the saturation of the cGMP-binding sites in PKG. After incubation, the samples were cooled to 4° C. and divided into 200 μl aliquots per tube. The addition of 100-fold excess unlabeled cGMP at time 0 sec (Bo) initiated the dissociation (exchange) of the bound [$^3$H]cGMP. The cGMP exchange in each tube was stopped at the appropriate time point by the addition of 2 ml of cold aqueous saturated $(NH_4)_2SO_4$. The samples were filtered, washed, and the portion of bound [³H]cGMP at any time point was determined, as described previously.

Results

To test the predictions made by the homology model, the influence of nitrative stress on the affinity of PKG-1α for cGMP were assessed by performing [³H]cGMP binding studies. PASMC were transiently transfected with expression plasmids containing WT-PKG-1α or Y247F-PKG-1α for 48 h. The cells were then serum starved for 4 h then exposed or not to SIN-1 (500 µM, 30 min) and PKG-1α immunoprecipitated. The PKG protein was immunopurified and assays were performed in the presence of increasing concentrations of [³H]cGMP. Immunoprecipitated WT-PKG-1α and Y247F-PKG-1α protein (100 ng) was analyzed in a [³H]cGMP binding assay (FIG. 6A) and a [³H]cGMP dissociation assay (FIG. 6B). In the dissociation assay a 100-fold excess of unlabeled cGMP was added at time 0 sec (Bo) to initiate the dissociation (exchange) of bound [³H]cGMP. The reaction was stopped with cold aqueous saturated (NH4)2SO4 at various time points. The results were plotted as ln (B/Bo) with Bo as the initial [[³H]cGMP bound] and B as the [[³H]cGMP remaining bound] at various time points. Enzyme kinetics were also determined using varying concentrations of cGMP (0-10 µM). The change in the enzyme activity for each concentration of cGMP was plotted in pmol/min/µg protein using nonlinear regression (curve fit) analysis.

Figure 6A:
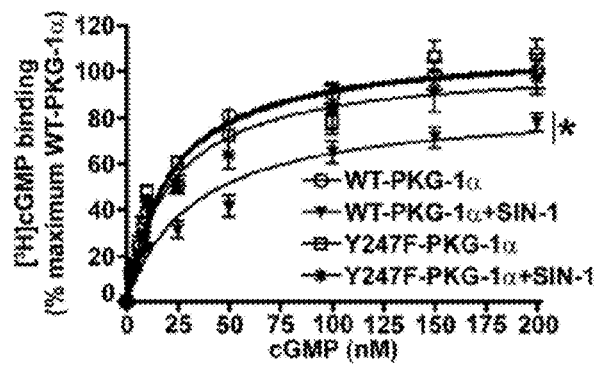
FIGS. 6A-6C are line graphs.
Figure 6B:
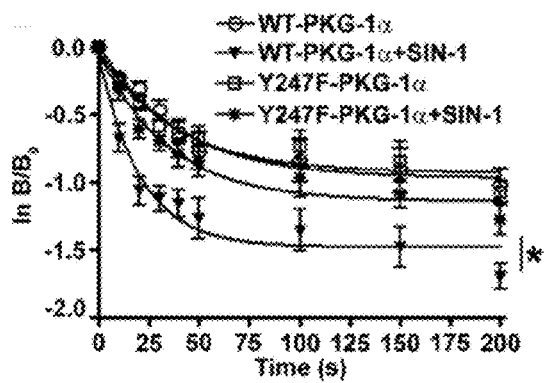

In the absence of SIN-1, the cGMP-binding stoichiometry of the Y247F-PKG-1α mutant was comparable with that of the WT-PKG-1α (FIG. 6A). However, the Kd values obtained for the WT-PKG-1α after SIN-1 treatment were higher than those obtained from the SIN-1 treated Y247F mutant (FIG. 6A, Table 2). The Kd values derived from these experiments were an average affinity of the two cGMP-binding sites within PKG-1α, and the binding characteristics of the individual sites, A and B, could not be assessed. To further confirm these results, a second measure of affinity was performed using cGMP exchange/dissociation analysis of the WT- and the Y247F-PKG-1α.

In the absence of SIN-1, the results demonstrated that the [³H]cGMP exchange/dissociation was biphasic (rapid vs. slow exchange) in the WT- and in the Y247F-PKG-1α dissociation curves, consistent with the presence of two kinetically distinct cGMP binding sites (sites A and B). However, SIN-1 exposure enhanced [³H]cGMP exchange/dissociation from the WT-PKG-1α but not from the Y247F mutant (FIG. 6B, Table 2). Further, SIN-1 decreased the dissociation/exchange rate (t½), or the time required for cGMP to dissociate from half the binding sites on PKG-Iα in the WTPKG-1α, from 27.06 s to 14.22 s, while no change was observed in the Y247F mutant (Table 2).

Figure 6C:
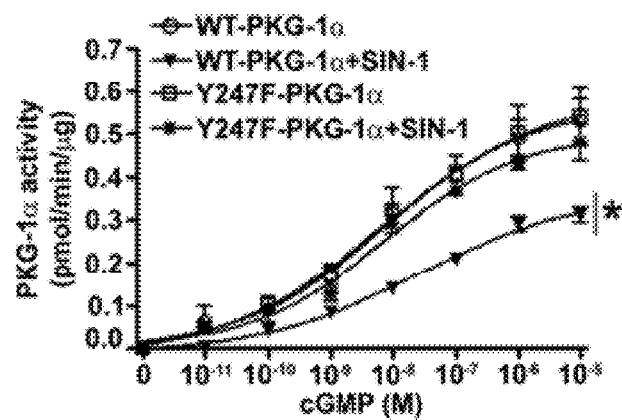

The cGMP binding and dissociation studies indicated that the phosphotransferase reaction catalyzed by PKG-1α may require a higher concentration of cGMP to reach the maximum velocity (Vmax) under nitrative stress. Therefore, Michaelis-Menten kinetics were performed to determine the cGMP concentrations required for PKG-1α to achieve half of the maximum velocity (Km). Utilizing a nonlinear regression curve it was demonstrated that, at constant ATP levels (125 µM) and varying cGMP concentrations (0-10 µM), SIN-1 challenge decreased the Vmax of the reaction of the WT-, but not of the Y247F mutant, PKG-1α from 0.47 to 0.28 pmols/min/m protein (FIG. 6C and Table 2). Further, the results showed that the Michaelis-Menten constant (Km) increased from 2.73 to 8.91 nM for cGMP in the WT-PKG-1α upon SIN-1 treatment, while no significant change was observed in the Y247F mutant (FIG. 6C and Table 2).

TABLE 2

|  | $K_d$ (nM) | $T_{1/2}$ (s) | $V_{max}$ (pmol/min/ µg) | $K_m$ (nM) |
|---|---|---|---|---|
| WT-PKG-1α | 21.34 ± 2.2 | 27.06 | 0.47 ± 0.02 | 2.73 ± 0.99 |
| WT-PKG-1α + SIN1 | 32.12 ± 5.5 | 14.22 | 0.28 ± 0.01 | 8.91 ± 2.69 |
| Y247F-PKG-1α | 20.43 ± 2.8 | 26.02 | 0.47 ± 0.02 | 2.43 ± 1.03 |
| Y247F-PKG-1α + SIN1 | 21.54 ± 3.4 | 23.79 | 0.42 ± 0.01 | 3.26 ± 0.99 |

In conclusion, SIN-1 treatment significantly attenuated maximal [³H]cGMP binding to WT-PKG-1α, but not to the Y247F-PKG-1α mutant (FIG. 6A). SIN-1 treatment enhanced the dissociation/exchange of [³H]cGMP from WT-PKG-1α, but not from Y247F-PKG-1α (FIG. 6B). The maximum velocity (Vmax) of the phosphotransferase reaction of WT-PKG-1α, but not Y247F-PKG-1α, was significantly decreased with SIN-1 exposure (FIG. 6C).

Tyrosine nitration is a selective process as not all tyrosine residues in a protein undergo nitration under patho-physiological conditions (Ischiropoulos, H., *Biochemical and Biophysical Research Communications* 305, 776-783 (2003)). PKG-1α has 21 tyrosine residues in its monomeric structure, of which 9 tyrosines are located in the regulatory domain and 12 are part of the catalytic domain. Using MS and mutational studies discussed above, it was discovered that nitration of tyrosine 247, located within the cGMP binding site B of the regulatory domain of PKG-1α, is responsible for the impaired kinase activity. Nitrative stress only decreased the cGMP dependent kinase activity, while basal PKG activity was unchanged.

Cyclic GMP binding to both sites A and B of PKG brings about a conformational change necessary for full kinase activity. The two cGMP binding sites share approximately 37% amino acid sequence similarity but differ in their cGMP binding kinetics (Corbin, J. D., et al., *The Journal of Biological Chemistry* 261, 1208-1214 (1986)). This difference may be due to the number of hydrogen bonds between cGMP and the cGMP binding sites on PKG as well as the length of these bonds (Kim, J. J., et al., *PloS One* 6, e18413). Molecular dynamic simulations using a full-length PKG-1α homology model predicted that the nitration of Y247 impairs hydrogen bonding between cGMP and the cGMP binding site B of the kinase. These results were confirmed by in vitro [³H]cGMP binding studies and reveal a mechanism by which PKG is regulated by nitrative stress. The findings are also in agreement with other studies which have also shown that the negative charge imparted by nitration alters the hydrogen bonding network between the substrate and protein in such enzymes as manganese superoxide dismutase (MnSOD) (Redondo-Horcajo, M., et al., *Cardiovascular Research* 87, 356365), glutathione reductase (Savvides, S. N., et al., *The Journal of Biological Chemistry* 277, 2779-2784 (2002)), and prostacyclin synthase (Nie, H., et al., *Diabetes* 55, 31333141 (2006)).

However, it should be noted that the results appear to be contradictory to a previous study that demonstrated that SIN-1 treatment decreased both basal and cGMP dependent PKG activity in VSMC (3). In this study single tyrosine to phenylalanine mutations of all tyrosine residues located in the catalytic domain of human PKG-1α were generated and Y345F- and the Y549F-PKG-1α mutants were found to be resistant to nitration dependent inhibition (3). Several differences between these studies may explain these apparently conflicting findings. Firstly, the presence of PKG-1β in VSMC may account for the decrease in the total basal PKG activity upon exposure to SIN-1 compared to PKG-1α expressed in Hek293 cells in the experiments. Secondly, Y345 in PKG-1α is located in the hinge/switch region (aa 328-355) between the regulatory and the catalytic domain, and acts as a tether for the catalytic domain (30). Mutations in this switch region have been shown to cause the kinase to be more active, presumably independent of cGMP (30). Finally, based on the homology model, Y549 of PKG-1α is located within the catalytic domain and interacts with the pseudo-substrate site, maintaining the enzyme in an auto-inhibited state (49,50). The auto-inhibition of PKG-1α is relieved by the conformational change caused by either cGMP binding or auto-phosphorylation, which disrupts the auto-inhibitory interaction between the regulatory and catalytic domains (12,13,51). The structural alterations resulting from the replacement of the tyrosine with a phenylalanine at residue 549 could result in a conformational change, thereby relieving this basal inhibition. Under both these circumstances the nitration of Y247 observed in the study would not influence the kinase activity of these PKG-1α mutants as the data indicate that the nitration of Y247 inhibits only the cGMP-inducible activation of PKG-1α.

In summary, Examples 1-7 indicate that the nitration of PKG-1α may be a common mechanism underlying vascular dysfunction in pulmonary hypertension and other disorders.

This conclusion is supported by other studies (Negash, et al., *American Journal of Physiology* 293, L1012-1020 (2007); Zhao, et al., *The Journal of Clinical Investigation* 119, 2009-2018 (2009)). Examples 1-7 show that Y247 as the primary target of nitrosative stress and is responsible for the attenuation of PKG-1α catalytic activity. Further, increasing intracellular cGMP levels has been used as a management strategy in patients with multiple vascular abnormalities including inhaled NO therapy for pulmonary hypertension; NO donors, such as nitroglycerin, isosorbide dinitrate, or isosorbide mononitrate for coronary artery diseases; cGMP specific phosphodiesterase-5 inhibitors, sildenafil and tadalafil for the treatment of pulmonary hypertension and erectile dysfunction; and B-type natriuretic peptides for hypoxemic respiratory failure. The major goal of these therapies is to increase the production of cGMP or inhibit its breakdown and thereby increase vascular dilation. However, if the cellular levels of cGMP become too high this can interfere with normal cellular proliferation, cause DNA strand breaks, and/or base alterations that are potentially mutagenic (Weinberger, B., et al., *Toxicol Sci* 59, 5-16 (2001)) Therefore, based on the data presented herein, it is believed that strategies aimed at minimizing PKG-1α nitration may have adjunct therapeutic value in the treatment of vascular disorders. These strategies may include cell or protein specific targeting of antioxidants, development of nitration site shielding peptides, or perhaps enhancing the autophosphorylation of PKG-1 to minimize the external requirement of cGMP for the enzyme activation.

I claim:

1. An isolated monoclonal antibody or antigen binding fragment thereof for detecting nitrated PKG-1α comprising an antigen binding site that binds specifically to an epitope within the protein encoded by the amino acid sequence of SEQ ID NO:4, wherein the epitope comprises the nitrated tyrosine 247 of SEQ ID NO:4.

2. The monoclonal antibody or antigen binding fragment thereof of claim 1 wherein the epitope is a conformational epitope or a linear epitope.

3. The monoclonal antibody or antigen binding fragment thereof of claim 1, wherein the antibody or antigen binding fragment thereof is a single chain antibody.

4. The monoclonal antibody or antigen binding fragment thereof of claim 1, wherein the antibody or antigen binding fragment thereof is humanized.

5. The monoclonal antibody or antigen binding fragment thereof of claim 1, wherein the antigen binding fragment is an Fv, Fab, Fab', or F(ab')$_2$.

6. The monoclonal antibody or antigen binding fragment thereof of claim 1, wherein the antibody or antigen binding fragment thereof is bispecific.

7. The monoclonal antibody or antigen binding fragment thereof of claim 1, wherein the antibody or antigen binding fragment thereof further comprises a radioisotope, a fluorescent compound, a bioluminescent compound, biotin, a chemiluminescent compound, a metal chelator or an enzyme.

8. A method of detecting nitrated PKG-1α comprising detecting nitration of PKG-1α at position Y247 of SEQ ID NO:4 in a biological sample by contacting the biological sample with the monoclonal antibody of claim 1, wherein the monoclonal antibody of claim 1 comprises a detectable label; and detecting the detectable label.

9. The method of claim 8 wherein the detecting is carried out using mass spectrometry or an immunoassay.

10. The method of claim 8 wherein the immunoassay is selected from the group consisting of radioimmunoassays, ELISAs, immunoprecipitation assays, Western blot, fluorescent immunoassays, and immunohistochemistry.

11. A kit comprising the monoclonal antibody or antigen binding fragment thereof of claim 1.

* * * * *

UNITED STATES PATENT AND TRADEMARK OFFICE
CERTIFICATE OF CORRECTION

PATENT NO. : 9,551,711 B2
APPLICATION NO. : 14/502160
DATED : January 24, 2017
INVENTOR(S) : Stephen M. Black Page 1 of 1

It is certified that error appears in the above-identified patent and that said Letters Patent is hereby corrected as shown below:

In the Specification

Column 1, Line numbers 12-19, please correct the paragraph as follows:
This invention was made with government support under HL060190, HL067841, HL084739, and HL101902 awarded by the National Institutes of Health. The government has certain rights in the invention.

Signed and Sealed this
Twelfth Day of June, 2018

Andrei Iancu
*Director of the United States Patent and Trademark Office*

SEQUENCE LISTING

```
<160> NUMBER OF SEQ ID NOS: 8

<210> SEQ ID NO 1
<211> LENGTH: 671
<212> TYPE: PRT
<213> ORGANISM: Homo sapiens

<400> SEQUENCE: 1

Met Ser Glu Leu Glu Glu Asp Phe Ala Lys Ile Leu Met Leu Lys Glu
1               5                   10                  15

Glu Arg Ile Lys Glu Leu Glu Lys Arg Leu Ser Glu Lys Glu Glu Glu
            20                  25                  30

Ile Gln Glu Leu Lys Arg Lys Leu His Lys Cys Gln Ser Val Leu Pro
        35                  40                  45

Val Pro Ser Thr His Ile Gly Pro Arg Thr Thr Arg Ala Gln Gly Ile
    50                  55                  60

Ser Ala Glu Pro Gln Thr Tyr Arg Ser Phe His Asp Leu Arg Gln Ala
65                  70                  75                  80

Phe Arg Lys Phe Thr Lys Ser Glu Arg Ser Lys Asp Leu Ile Lys Glu
                85                  90                  95

Ala Ile Leu Asp Asn Asp Phe Met Lys Asn Leu Glu Leu Ser Gln Ile
            100                 105                 110

Gln Glu Ile Val Asp Cys Met Tyr Pro Val Glu Tyr Gly Lys Asp Ser
        115                 120                 125

Cys Ile Ile Lys Glu Gly Asp Val Gly Ser Leu Val Tyr Val Met Glu
    130                 135                 140

Asp Gly Lys Val Glu Val Thr Lys Glu Gly Val Lys Leu Cys Thr Met
145                 150                 155                 160

Gly Pro Gly Lys Val Phe Gly Glu Leu Ala Ile Leu Tyr Asn Cys Thr
                165                 170                 175
```

```
Arg Thr Ala Thr Val Lys Thr Leu Val Asn Val Lys Leu Trp Ala Ile
            180                 185                 190

Asp Arg Gln Cys Phe Gln Thr Ile Met Met Arg Thr Gly Leu Ile Lys
        195                 200                 205

His Thr Glu Tyr Met Glu Phe Leu Lys Ser Val Pro Thr Phe Gln Ser
    210                 215                 220

Leu Pro Glu Glu Ile Leu Ser Lys Leu Ala Asp Val Leu Glu Thr
225                 230                 235                 240

His Tyr Glu Asn Gly Glu Tyr Ile Ile Arg Gln Gly Ala Arg Gly Asp
                245                 250                 255

Thr Phe Phe Ile Ile Ser Lys Gly Thr Val Asn Val Thr Arg Glu Asp
            260                 265                 270

Ser Pro Ser Glu Asp Pro Val Phe Leu Arg Thr Leu Gly Lys Gly Asp
        275                 280                 285

Trp Phe Gly Glu Lys Ala Leu Gln Gly Glu Asp Val Arg Thr Ala Asn
    290                 295                 300

Val Ile Ala Ala Glu Ala Val Thr Cys Leu Val Ile Asp Arg Asp Ser
305                 310                 315                 320

Phe Lys His Leu Ile Gly Gly Leu Asp Asp Val Ser Asn Lys Ala Tyr
                325                 330                 335

Glu Asp Ala Glu Ala Lys Ala Lys Tyr Glu Ala Glu Ala Ala Phe Phe
            340                 345                 350

Ala Asn Leu Lys Leu Ser Asp Phe Asn Ile Ile Asp Thr Leu Gly Val
        355                 360                 365

Gly Gly Phe Gly Arg Val Glu Leu Val Gln Leu Lys Ser Glu Glu Ser
    370                 375                 380

Lys Thr Phe Ala Met Lys Ile Leu Lys Lys Arg His Ile Val Asp Thr
385                 390                 395                 400

Arg Gln Gln Glu His Ile Arg Ser Glu Lys Gln Ile Met Gln Gly Ala
                405                 410                 415

His Ser Asp Phe Ile Val Arg Leu Tyr Arg Thr Phe Lys Asp Ser Lys
            420                 425                 430

Tyr Leu Tyr Met Leu Met Glu Ala Cys Leu Gly Gly Glu Leu Trp Thr
        435                 440                 445

Ile Leu Arg Asp Arg Gly Ser Phe Glu Asp Ser Thr Thr Arg Phe Tyr
    450                 455                 460

Thr Ala Cys Val Val Glu Ala Phe Ala Tyr Leu His Ser Lys Gly Ile
465                 470                 475                 480

Ile Tyr Arg Asp Leu Lys Pro Glu Asn Leu Ile Leu Asp His Arg Gly
                485                 490                 495

Tyr Ala Lys Leu Val Asp Phe Gly Phe Ala Lys Lys Ile Gly Phe Gly
            500                 505                 510

Lys Lys Thr Trp Thr Phe Cys Gly Thr Pro Glu Tyr Val Ala Pro Glu
        515                 520                 525

Ile Ile Leu Asn Lys Gly His Asp Ile Ser Ala Asp Tyr Trp Ser Leu
    530                 535                 540

Gly Ile Leu Met Tyr Glu Leu Leu Thr Gly Ser Pro Pro Phe Ser Gly
545                 550                 555                 560

Pro Asp Pro Met Lys Thr Tyr Asn Ile Ile Leu Arg Gly Ile Asp Met
                565                 570                 575

Ile Glu Phe Pro Lys Lys Ile Ala Lys Asn Ala Ala Asn Leu Ile Lys
            580                 585                 590
```

```
Lys Leu Cys Arg Asp Asn Pro Ser Glu Arg Leu Gly Asn Leu Lys Asn
            595                 600                 605
Gly Val Lys Asp Ile Gln Lys His Lys Trp Phe Glu Gly Phe Asn Trp
        610                 615                 620
Glu Gly Leu Arg Lys Gly Thr Leu Thr Pro Ile Ile Pro Ser Val
625                 630                 635                 640
Ala Ser Pro Thr Asp Thr Ser Asn Phe Asp Ser Phe Pro Glu Asp Asn
            645                 650                 655
Asp Glu Pro Pro Pro Asp Asn Ser Gly Trp Asp Ile Asp Phe
        660                 665                 670

<210> SEQ ID NO 2
<211> LENGTH: 18
<212> TYPE: PRT
<213> ORGANISM: Homo sapiens

<400> SEQUENCE: 2

Leu Ala Asp Val Leu Glu Glu Thr His Tyr Glu Asn Gly Glu Tyr Ile
1               5                   10                  15

Ile Arg

<210> SEQ ID NO 3
<211> LENGTH: 16
<212> TYPE: PRT
<213> ORGANISM: Homo sapiens

<400> SEQUENCE: 3

Gln Ile Met Gln Gly Ala His Ser Asp Phe Ile Val Arg Leu Tyr Arg
1               5                   10                  15

<210> SEQ ID NO 4
<211> LENGTH: 671
<212> TYPE: PRT
<213> ORGANISM: Homo sapiens
<220> FEATURE:
<221> NAME/KEY: MISC_FEATURE
<222> LOCATION: (247)..(247)
<223> OTHER INFORMATION: Xaa = nitrated tyrosine

<400> SEQUENCE: 4

Met Ser Glu Leu Glu Glu Asp Phe Ala Lys Ile Leu Met Leu Lys Glu
1               5                   10                  15

Glu Arg Ile Lys Glu Leu Glu Lys Arg Leu Ser Glu Lys Glu Glu Glu
                20                  25                  30

Ile Gln Glu Leu Lys Arg Lys Leu His Lys Cys Gln Ser Val Leu Pro
            35                  40                  45

Val Pro Ser Thr His Ile Gly Pro Arg Thr Thr Arg Ala Gln Gly Ile
        50                  55                  60

Ser Ala Glu Pro Gln Thr Tyr Arg Ser Phe His Asp Leu Arg Gln Ala
65                  70                  75                  80

Phe Arg Lys Phe Thr Lys Ser Glu Arg Ser Lys Asp Leu Ile Lys Glu
                85                  90                  95

Ala Ile Leu Asp Asn Asp Phe Met Lys Asn Leu Glu Leu Ser Gln Ile
            100                 105                 110

Gln Glu Ile Val Asp Cys Met Tyr Pro Val Glu Tyr Gly Lys Asp Ser
        115                 120                 125

Cys Ile Ile Lys Glu Gly Asp Val Gly Ser Leu Val Tyr Val Met Glu
    130                 135                 140

Asp Gly Lys Val Glu Val Thr Lys Glu Gly Val Lys Leu Cys Thr Met
```

```
             145                 150                 155                 160
        Gly Pro Gly Lys Val Phe Gly Glu Leu Ala Ile Leu Tyr Asn Cys Thr
                        165                 170                 175

Arg Thr Ala Thr Val Lys Thr Leu Val Asn Val Lys Leu Trp Ala Ile
                        180                 185                 190

Asp Arg Gln Cys Phe Gln Thr Ile Met Met Arg Thr Gly Leu Ile Lys
                        195                 200                 205

His Thr Glu Tyr Met Glu Phe Leu Lys Ser Val Pro Thr Phe Gln Ser
            210                 215                 220

Leu Pro Glu Glu Ile Leu Ser Lys Leu Ala Asp Val Leu Glu Glu Thr
        225                 230                 235                 240

His Tyr Glu Asn Gly Glu Xaa Ile Ile Arg Gln Gly Ala Arg Gly Asp
                        245                 250                 255

Thr Phe Phe Ile Ile Ser Lys Gly Thr Val Asn Val Thr Arg Glu Asp
                        260                 265                 270

Ser Pro Ser Glu Asp Pro Val Phe Leu Arg Thr Leu Gly Lys Gly Asp
                        275                 280                 285

Trp Phe Gly Glu Lys Ala Leu Gln Gly Glu Asp Val Arg Thr Ala Asn
                        290                 295                 300

Val Ile Ala Ala Glu Ala Val Thr Cys Leu Val Ile Asp Arg Asp Ser
        305                 310                 315                 320

Phe Lys His Leu Ile Gly Gly Leu Asp Asp Val Ser Asn Lys Ala Tyr
                        325                 330                 335

Glu Asp Ala Glu Ala Lys Ala Lys Tyr Glu Ala Glu Ala Ala Phe Phe
                        340                 345                 350

Ala Asn Leu Lys Leu Ser Asp Phe Asn Ile Ile Asp Thr Leu Gly Val
                        355                 360                 365

Gly Gly Phe Gly Arg Val Glu Leu Val Gln Leu Lys Ser Glu Glu Ser
                        370                 375                 380

Lys Thr Phe Ala Met Lys Ile Leu Lys Lys Arg His Ile Val Asp Thr
        385                 390                 395                 400

Arg Gln Gln Glu His Ile Arg Ser Glu Lys Gln Ile Met Gln Gly Ala
                        405                 410                 415

His Ser Asp Phe Ile Val Arg Leu Tyr Arg Thr Phe Lys Asp Ser Lys
                        420                 425                 430

Tyr Leu Tyr Met Leu Met Glu Ala Cys Leu Gly Gly Glu Leu Trp Thr
                        435                 440                 445

Ile Leu Arg Asp Arg Gly Ser Phe Glu Asp Ser Thr Thr Arg Phe Tyr
                        450                 455                 460

Thr Ala Cys Val Val Glu Ala Phe Ala Tyr Leu His Ser Lys Gly Ile
        465                 470                 475                 480

Ile Tyr Arg Asp Leu Lys Pro Glu Asn Leu Ile Leu Asp His Arg Gly
                        485                 490                 495

Tyr Ala Lys Leu Val Asp Phe Gly Phe Ala Lys Lys Ile Gly Phe Gly
                        500                 505                 510

Lys Lys Thr Trp Thr Phe Cys Gly Thr Pro Glu Tyr Val Ala Pro Glu
                        515                 520                 525

Ile Ile Leu Asn Lys Gly His Asp Ile Ser Ala Asp Tyr Trp Ser Leu
                        530                 535                 540

Gly Ile Leu Met Tyr Glu Leu Leu Thr Gly Ser Pro Pro Phe Ser Gly
        545                 550                 555                 560

Pro Asp Pro Met Lys Thr Tyr Asn Ile Ile Leu Arg Gly Ile Asp Met
                        565                 570                 575
```

```
Ile Glu Phe Pro Lys Lys Ile Ala Lys Asn Ala Ala Asn Leu Ile Lys
            580                 585                 590

Lys Leu Cys Arg Asp Asn Pro Ser Glu Arg Leu Gly Asn Leu Lys Asn
        595                 600                 605

Gly Val Lys Asp Ile Gln Lys His Lys Trp Phe Glu Gly Phe Asn Trp
610                 615                 620

Glu Gly Leu Arg Lys Gly Thr Leu Thr Pro Ile Ile Pro Ser Val
625                 630                 635                 640

Ala Ser Pro Thr Asp Thr Ser Asn Phe Asp Ser Phe Pro Glu Asp Asn
                645                 650                 655

Asp Glu Pro Pro Pro Asp Asp Asn Ser Gly Trp Asp Ile Asp Phe
                660                 665                 670

<210> SEQ ID NO 5
<211> LENGTH: 15
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa = nitrated tyrosine

<400> SEQUENCE: 5

Glu Asn Gly Glu Xaa Ile Ile Arg Gln Gly Ala Arg Gly Asp Cys
1               5                   10                  15

<210> SEQ ID NO 6
<211> LENGTH: 671
<212> TYPE: PRT
<213> ORGANISM: Homo sapiens
<220> FEATURE:
<221> NAME/KEY: MISC_FEATURE
<222> LOCATION: (425)..(425)
<223> OTHER INFORMATION: Xaa = nitrated tyrosine

<400> SEQUENCE: 6

Met Ser Glu Leu Glu Glu Asp Phe Ala Lys Ile Leu Met Leu Lys Glu
1               5                   10                  15

Glu Arg Ile Lys Glu Leu Glu Lys Arg Leu Ser Glu Lys Glu Glu Glu
            20                  25                  30

Ile Gln Glu Leu Lys Arg Lys Leu His Lys Cys Gln Ser Val Leu Pro
        35                  40                  45

Val Pro Ser Thr His Ile Gly Pro Arg Thr Thr Arg Ala Gln Gly Ile
    50                  55                  60

Ser Ala Glu Pro Gln Thr Tyr Arg Ser Phe His Asp Leu Arg Gln Ala
65                  70                  75                  80

Phe Arg Lys Phe Thr Lys Ser Glu Arg Ser Lys Asp Leu Ile Lys Glu
                85                  90                  95

Ala Ile Leu Asp Asn Asp Phe Met Lys Asn Leu Glu Leu Ser Gln Ile
            100                 105                 110

Gln Glu Ile Val Asp Cys Met Tyr Pro Val Glu Tyr Gly Lys Asp Ser
        115                 120                 125

Cys Ile Ile Lys Glu Gly Asp Val Gly Ser Leu Val Tyr Val Met Glu
    130                 135                 140

Asp Gly Lys Val Glu Val Thr Lys Glu Gly Val Lys Leu Cys Thr Met
145                 150                 155                 160

Gly Pro Gly Lys Val Phe Gly Glu Leu Ala Ile Leu Tyr Asn Cys Thr
                165                 170                 175
```

-continued

```
Arg Thr Ala Thr Val Lys Thr Leu Val Asn Val Lys Leu Trp Ala Ile
            180                 185                 190
Asp Arg Gln Cys Phe Gln Thr Ile Met Met Arg Thr Gly Leu Ile Lys
        195                 200                 205
His Thr Glu Tyr Met Glu Phe Leu Lys Ser Val Pro Thr Phe Gln Ser
    210                 215                 220
Leu Pro Glu Glu Ile Leu Ser Lys Leu Ala Asp Val Leu Glu Glu Thr
225                 230                 235                 240
His Tyr Glu Asn Gly Glu Tyr Ile Ile Arg Gln Gly Ala Arg Gly Asp
                245                 250                 255
Thr Phe Phe Ile Ile Ser Lys Gly Thr Val Asn Val Thr Arg Glu Asp
            260                 265                 270
Ser Pro Ser Glu Asp Pro Val Phe Leu Arg Thr Leu Gly Lys Gly Asp
        275                 280                 285
Trp Phe Gly Glu Lys Ala Leu Gln Gly Glu Asp Val Arg Thr Ala Asn
    290                 295                 300
Val Ile Ala Ala Glu Ala Val Thr Cys Leu Val Ile Asp Arg Asp Ser
305                 310                 315                 320
Phe Lys His Leu Ile Gly Gly Leu Asp Asp Val Ser Asn Lys Ala Tyr
                325                 330                 335
Glu Asp Ala Glu Ala Lys Ala Lys Tyr Glu Ala Glu Ala Ala Phe Phe
            340                 345                 350
Ala Asn Leu Lys Leu Ser Asp Phe Asn Ile Ile Asp Thr Leu Gly Val
        355                 360                 365
Gly Gly Phe Gly Arg Val Glu Leu Val Gln Leu Lys Ser Glu Glu Ser
    370                 375                 380
Lys Thr Phe Ala Met Lys Ile Leu Lys Lys Arg His Ile Val Asp Thr
385                 390                 395                 400
Arg Gln Gln Glu His Ile Arg Ser Glu Lys Gln Ile Met Gln Gly Ala
                405                 410                 415
His Ser Asp Phe Ile Val Arg Leu Xaa Arg Thr Phe Lys Asp Ser Lys
            420                 425                 430
Tyr Leu Tyr Met Leu Met Glu Ala Cys Leu Gly Gly Glu Leu Trp Thr
        435                 440                 445
Ile Leu Arg Asp Arg Gly Ser Phe Glu Asp Ser Thr Thr Arg Phe Tyr
    450                 455                 460
Thr Ala Cys Val Val Glu Ala Phe Ala Tyr Leu His Ser Lys Gly Ile
465                 470                 475                 480
Ile Tyr Arg Asp Leu Lys Pro Glu Asn Leu Ile Leu Asp His Arg Gly
                485                 490                 495
Tyr Ala Lys Leu Val Asp Phe Gly Phe Ala Lys Lys Ile Gly Phe Gly
            500                 505                 510
Lys Lys Thr Trp Thr Phe Cys Gly Thr Pro Glu Tyr Val Ala Pro Glu
        515                 520                 525
Ile Ile Leu Asn Lys Gly His Asp Ile Ser Ala Asp Tyr Trp Ser Leu
    530                 535                 540
Gly Ile Leu Met Tyr Glu Leu Leu Thr Gly Ser Pro Pro Phe Ser Gly
545                 550                 555                 560
Pro Asp Pro Met Lys Thr Tyr Asn Ile Ile Leu Arg Gly Ile Asp Met
                565                 570                 575
Ile Glu Phe Pro Lys Lys Ile Ala Lys Asn Ala Ala Asn Leu Ile Lys
            580                 585                 590
Lys Leu Cys Arg Asp Asn Pro Ser Glu Arg Leu Gly Asn Leu Lys Asn
```

-continued

```
                595                 600                 605
Gly Val Lys Asp Ile Gln Lys His Lys Trp Phe Glu Gly Phe Asn Trp
        610                 615                 620

Glu Gly Leu Arg Lys Gly Thr Leu Thr Pro Pro Ile Ile Pro Ser Val
625                 630                 635                 640

Ala Ser Pro Thr Asp Thr Ser Asn Phe Asp Ser Phe Pro Glu Asp Asn
                645                 650                 655

Asp Glu Pro Pro Pro Asp Asp Asn Ser Gly Trp Asp Ile Asp Phe
        660                 665                 670

<210> SEQ ID NO 7
<211> LENGTH: 18
<212> TYPE: PRT
<213> ORGANISM: Homo sapiens
<220> FEATURE:
<221> NAME/KEY: MISC_FEATURE
<222> LOCATION: (15)..(15)
<223> OTHER INFORMATION: Xaa = 3-nitrotyrosine from the PKG-1 alpha
      sequence

<400> SEQUENCE: 7

Leu Ala Asp Val Leu Glu Glu Thr His Tyr Glu Asn Gly Glu Xaa Ile
1               5                   10                  15

Ile Arg

<210> SEQ ID NO 8
<211> LENGTH: 15
<212> TYPE: PRT
<213> ORGANISM: Homo sapiens

<400> SEQUENCE: 8

Glu Asn Gly Glu Tyr Ile Ile Arg Gln Gly Ala Arg Gly Asp Cys
1               5                   10                  15
```